US008268846B2

(12) United States Patent
Wakefield et al.

(10) Patent No.: US 8,268,846 B2
(45) Date of Patent: Sep. 18, 2012

(54) AMINO HETEROCYCLIC LINKED PYRIMIDINE DERIVATIVES

(75) Inventors: Brian D. Wakefield, Vernon Hills, IL (US); Robert J. Altenbach, Chicago, IL (US); Lawrence A. Black, Libertyville, IL (US); Marlon D. Cowart, Round Lake Beach, IL (US); Irene Drizin, Wadsworth, IL (US); Huaqing Liu, Buffalo Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 467 days.

(21) Appl. No.: 12/501,137

(22) Filed: Jul. 10, 2009

(65) Prior Publication Data

US 2010/0016344 A1  Jan. 21, 2010

Related U.S. Application Data

(60) Provisional application No. 61/079,983, filed on Jul. 11, 2008.

(51) Int. Cl.
*C07D 487/04* (2006.01)
*A61K 31/505* (2006.01)
(52) U.S. Cl. ............... 514/267; 544/249; 544/250
(58) Field of Classification Search ............ 544/249, 544/250; 514/267
See application file for complete search history.

(56) References Cited

U.S. PATENT DOCUMENTS

2008/0188452 A1* 8/2008 Altenbach et al. ....... 514/210.16

FOREIGN PATENT DOCUMENTS

WO  WO2007090854 A1  8/2007

OTHER PUBLICATIONS

Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition and Expanded, pp. 451 and 596.*
Silverman, Prodrugs and Drug Delivery Systems, The Organic Chemistry of Drug Design and Drug Action, pp. 352-399, 1992.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Robinson, Medical Therapy of Inflammatory Bowel Disease for the 21st Century, Eur J Suppl 582, pp. 90-98, 1998.*
Singh et al., Immune Therapy in inflammatory bowel disease and models of colitis, British Journal of Surgery, 88, pp. 1558-1569, 2001.*
Esch et al., The Histamine H4 receptor as a new therapeutic target for inflammation, Trends in Pharmacological Sciences, vol. 26, No. 9, pp. 462-469, Sep. 2005.*
Gantner et al., Histamine H4 and H2 Receptors Control Histamine-Induced Interleukin-16 Release from Human CD8+ T Cells, The Journal of Pharmacology and Experimental Therapeutics, vol. 303, No. 1, pp. 300-307, 2002.*
Akdis et al., "Histamine receptors are hot in immunopharmacology", European Journal of Pharmacology, 2006, 533, 69-76.
Bell et al.,"Involvement of histamine H4 and H1 receptors in scratching induced by histamine receptor agonists in Balb C mice." British Journal of Pharmacology, 2004, 142, 374-380.
Bennett et al. "A peripheral mononeuropathy in rat that produces disorders of pain sensation like those seen in man", Pain, 1988, 33, 87-107.
Buckland et al., "Histamine induces cytoskeletal changes in human eosinophils via the H(4) receptor", British Journal of Pharmacology, 2003, 140, 1117-1127.
Chaplan S. R. et al., "Quantitative assessment of tactile allodynia in the rat paw," Journal of Neuroscience Methods, 1994, vol. 53, pp. 55-63.
Cianchi et al., "The role of cyclooxygenase-2 in mediating the effects of histamine on cell proliferation and vascular endothelial growth factor production in colorectal cancer," Clinical Cancer Research, 2005, 11 (19), 6807-6815.
Coge et al., "Structure and Expression of the Human Histamine H4-Receptor Gene", Biochemical and Biophysical Research Communications, 2001, 284, 301-309.
Collins et al., "Emerging therapies for neuropathic pain", Expert Opinion on Emerging Drugs, 2005, 10 (1), 95-108.
Coruzzi et al., Antiinflammatory and antinociceptive effects of the selective histamine H4-receptor antagonists JNJ7777120 and VUF6002 in a rat model of carrageenan-induced acute inflammation, European Journal of Pharmacology, 2007, 563, 240-244.
Coruzzi et al., "Gastric Effects of the Histamine H4 Receptor Antagonists JNJ7777120 and VUF6002" 35th Mtg of the European Histamine Research Society in Delphi, Greece (May 10-13, 2006) presentation O44.
de Esch I.J.P. et al., "The histamine H4 Receptor as a new therapeutic target for inflammation", Trends in Pharmacological Science, 2005, 26 (9), 462-469.
Dixon W. J. et al., "Efficient analysis of experimental observations," Annual Review of Pharmacology and Toxicology, 1980, vol. 20, pp. 441-462.
Dray et al., "Pharmacology of chronic pain", Trends in Pharmacological Sciences, 1994, 15 (6), 190-197.
Dunford et al.,"The histamine H4 receptor mediates allergic airway inflammation by regulating the activation of CD4+ T cells," The Journal of Immunology, 2006, 176, 7062-7070.

(Continued)

*Primary Examiner* — Deepak Rao
(74) *Attorney, Agent, or Firm* — Nancy J. Gettel; Portia Chen

(57) ABSTRACT

Macrocyclic benzofused pyrimidine compounds, compositions comprising such compounds, methods for making the compounds, and methods of treating and preventing the progression of diseases, conditions and disorders using such compounds and compositions are described herein.

6 Claims, No Drawings

OTHER PUBLICATIONS

Dworkin R. et al., "An Overview of Neuropathic Pain: Syndromes, Symptoms, Signs, and Several Mechanisms", Clinical Journal of Pain, 2002, 18 (6), 343-349.

Esbenshade et al., "Pharmacological and behavioral properties of A-349821, a selective and potent human histamine H3 receptor antagonist", Biochemical Pharmacology, 2004, 68, 933-945.

Fogel et al., "Influence of H3/H4 Receptor Antagonist Thioperamide on Regional Haemodynamics in Rats with Trinitrobenzene Sulfonic Acid-Induced Colitis" 35th Mtg of the European Histamine Research Society in Delphi, Greece (May 10-13, 2006), P32.

Grzybowska-Kowalczyk et al., "Human and clinical aspects of histamine: Distribution pattern of histamine H4 receptor in human synovial tissue from patients with rheumatoid arthritis", Inflammation Research, 2007, 56, Supplement 1, S59-S60.

Hartwig, et al., "Room-Temperature Palladium-Catalyzed Amination of Aryl Bromides and Chloride and Extended Scope of Aromatic C-N Bond Formation with a Commercial Ligand," J. Org . Chem., 1999, vol. 64 (15), pp. 5575-5580.

Hartwig, J. et al., "Transition Metal Catalyzed Synthesis of Arylamines and Aryl Ethers from Aryl Halides and Triflates: Scope and Mechanism," Angew Chem Mt Ed,, 1998, vol. 37, 2046-2067.

Higuchi T., et al., "Pro-Drugs as Novel Drug Delivery Systems (ACS Symposium Series, 14)," American Chemical Society, 1975, Table of Contents.

Honore et al., "Interleukin-1 alpha beta gene-deficient mice show reduced nociceptive sensitivity in models of inflammatory and neuropathic pain but not post-operative pain", Behavioural Brain Research, 2006, 167, 355-364.

Igaz et al., in Histamine: Biology and Medical Aspects, 2004, 89-96.

Ikawa, et al., "Histamine H4 receptor expression in human synovial cells obtained from patients suffering from rheumatoid arthritis,"Biol. Pharm. Bull., 2005, vol. 28 (10), pp. 2016-2018.

IUPAC Commission on Nomenclature of Organic Chemistry: Rules for the Nomenclature of Organic Chemistry Section E: Stereochemistry, Pure Appl Chem, 1976, 45, 11-30.

Jablonowska et al., "Distribution pattern of histamine H4 receptor in human synovial tissue from patients with rheumatoid arthritis" 35th Mtg of the European Histamine Research Society in Delphi, Greece (May 10-13, 2006), presentation 036.

Joshi et al., "Animal models of pain for drug discovery", Expert Opinion on Drug Discovery, 2006, 1, 323-334.

Joshi et al., "Involvement of the TTX-resistant sodium channel Nav 1.8 in inflammatory and neuropathic, but not post-operative, pain states", Pain, 2006, 123, 75-82.

Kim S. H. et al., "An experimental model for peripheral neuropathy produced by segmental spinal nerve ligation in the rat," Pain, 1992, vol. 50 (3), pp. 355-363.

Kiyomori A. et al., "An Efficient Copper-Catalyzed Coupling of Aryl Halides with Imidazoles," Tet Lett, 1999, 40, pp. 2657-2660.

Klapars A. et al., "A General and Efficient Copper Catalyst for the Amidation of Aryl Halides and the N-Arylation of Nitrogen Heterocycles", J. Amer. Chem. Soc. 2001, 123, pp. 7727-7729.

Krueger K.M. et al., "G Protein-Dependent Pharmacology of Histamine H.sub.3 Receptor ligands: Evidence for Heterogeneous Active State Receptor Conformations", Journal of Pharmacology and Experimental Therapeutics, 2005, 314 (1), 271-281.

Kwong, F.Y. et al., "Copper-Catalyzed Coupling of Alkylamines and Aryl Iodides: An Efficient System Even in an Air Atmosphere," Org Lett, 2002, vol. 4, 581-584.

Liu, et al., "Cloning and Pharmacological Characterization of a Fourth Histamine Receptor (H4) Expressed in Bone Marrow", Molecular Pharmacology, 2001, 59, 420-426.

Liu et al., "Comparison of Human, Mouse, Rat, and Guinea Pig Histamine H4 Receptors Reveals Substantial Pharmacological Species Variation", Journal of Pharmacology and Experimental Therapeutics, 2001, 299, 121-130.

Maslinska, et al., "Toll-like receptors (TLRs) and histamine receptor H4 in articular tissues of patients with rheumatoid arthritis (RA)" 34th Mtg of the European Histamine Research Society in Bled, Slovenia (May 11-15, 2005), Poster P-03.

Nguyen, et al., "Discovery of a Novel Member of the Histamine Receptor Family", Molecular Pharmacology, 2001, 59, 427-433.

Oda et al.,"Molecular cloning of monkey histamine H4 receptor.," Journal of the Pharmacological Society, 2005, 98, 319-322.

Parsons et al., "Histamine and its receptors", British Journal of Pharmacology, 2006, 147, S127-S135.

Porreca et al., "Antinociceptive Pharmacology of N-[[4-(4,5-Dihydro-1H-imidazol-2-yl)phenylmethyl]-242-[[(4-methoxy-2,6-dimethylphenyl)sulfonyl]methylaminojethoxyl-N-methylacetamide, Fumarate (LF22-0542), a Novel Nonpeptidic Bradykinin B1 Receptor Antagonist", Journal of Pharmacology and Experimental Therapeutics, 2006, 318, 195-205.

Smith et al., "Neuropathic Pain and the Electrophysiology and Pharmacology of Nerve Injury", Drug Develop. Research, 2001, 54 (3), 140-153.

Smith et al., Vogel's Textbook of Practical Organic Chemistry, 1989, Ed. 5, Longman Scientific & Technical.

Stark., "Recent advances in histamine H3/H4 receptor ligands," Expert Opinion in Therapeutic Patents, 2003, vol. 13 (6), pp. 851-865.

Sugahara M. et al., "A Facile Copper-Catalyzed Ullmann Condensation: N-Arylation of Heterocyclic Compounds Containing an -NHCO- Moiety", Chem Pharm Bull 1997, vol. 45, 719-721.

Thurmond et al., "A Potent and Selective Histamine H4 Receptor Antagonist with Anti-Inflammatory Properties", Journal of Pharmacology and Experimental Therapeutics, 2004, 309, 404-413.

Varga et al.,"Inhibitory effects of histamine H4 receptor antagonists on experimental colitis in the rat.," European Journal of Pharmacology, 2005, 522, 130-138.

Vinik et al., "Diabetic neuropathies", Medical Clinics of North America, 2004, 88 (4), 947-999.

Vogel G., et al., Drug Discovery and Evaluation, 2nd edition, 2002, Springer-Verlag, New York, pp. 702-706.

Wolfe J.P. et al., "Rational Development of Practical Catalysts for Aromatic Carbon-Nitrogen Bond Formation," Ace Chem Res,, 1998, vol. 13, 805-818.

Wolfe J.P. et al., "Simple, Efficient Catalyst System for the Palladium-Catalyzed Amination of Aryl Chlorides, Bromides, and Triflates," J.Org.Chem., 2000, vol. 65, 1158-1174.

Yamamoto T et al., Palladium Catalyzed Conjugate 1,4-Addition of Organoboronic Acids to alpha, beta Unsaturated Ketones, Chemistry Letters, 2006, 35 (2), 198.

Yang B.H. et al., "Palladium-catalyzed amination of aryl halides and sulfonates," J.Organomet.Chem,, 1999, vol. 576, 125-146.

Zhu, et al., "Cloning, Expression, and Pharmacological Characterization of a Novel Human Histamine Receptor", Molecular Pharmacology, 2001, 59, 434-441.

* cited by examiner

AMINO HETEROCYCLIC LINKED PYRIMIDINE DERIVATIVES

CROSS-REFERENCE TO RELATED APPLICATIONS

This patent application claims priority to U.S. Provisional Patent Application No. 61/079,983, filed on Jul. 11, 2008, the entirety of which is incorporated herein by reference.

BACKGROUND OF THE INVENTION

1. Technical Field

The invention relates to amino heterocyclic linked pyrimidine compounds, compositions comprising such compounds, methods for making the compounds, and methods of treating conditions and disorders using such compounds and compositions.

2. Description of Related Technology

Histamine modulates a number of physiological activities, acting through specific histamine receptors (reviewed in Parsons and Ganellin, British Journal of Pharmacology (2006) 147, S127-S135; Igaz and Hegyesi, in Histamine: Biology and Medical Aspects (2004), 89-96; Editor(s): A. Falus; Published S. Karger A G, Basel). Four histamine receptors have been identified as playing distinct physiological roles. These are the histamine $H_1$ receptor, the histamine $H_2$ receptor, the histamine $H_3$ receptor, and the histamine $H_4$ receptor. Compounds that modulate, or affect, the activity of these receptors may be used to treat diseases. For example, the well-known role of $H_1$ receptors in modulating allergic reaction has led to the clinical development of drugs that treat allergic rhinitis and other diseases by antagonizing the action of naturally-occurring, or endogenous, histamine in the body. Histamine $H_2$ receptor antagonists have been developed and proven clinically useful in treating diseases associated with excess stomach acidity. The histamine $H_3$ receptor is found predominantly on nerve terminals in the central nervous system (CNS) and the peripheral nervous system, i.e., periphery, and antagonists of this receptor have been documented in studies that benefit mammalian cognitive processes, improve wakefulness, suppress symptoms of allergic rhinitis, and suppress weight gain. The histamine $H_4$ receptor is the most recently identified histamine receptor and has been characterized as a distinct histamine receptor. The histamine $H_4$ receptor has been found in a number of mammalian tissues and has been determined to modulate a number of physiological processes, including immunological function.

By use of histamine $H_4$ ligands in animal disease models as well as in in vitro and ex vivo studies, the histamine $H_4$ receptor has been demonstrated to play an important role in various physiological and pathophysiological processes. Separately, in experiments with histamine $H_4$ deficient (knock out) animals and cells and tissues from such histamine $H_4$ deficient animals, the histamine $H_4$ receptor has been demonstrated to play an important role in various physiological and pathophysiological processes. Examples of diseases and disorders where histamine $H_4$ receptors have been found to play an important role include, for example, asthma, allergy, rheumatoid arthritis, and inflammation.

The activity of histamine $H_4$ receptors can be modified or regulated by the administration of histamine $H_4$ receptor ligands. The ligands can demonstrate antagonist, inverse agonist, or partial agonist activity.

Histamine $H_4$ ligands in different structural classes have been reviewed in (Schwartz, Expert Opinion in Therapeutic Patents (2003) vol. 13, pp. 851-865). It would be beneficial to provide additional compounds demonstrating $H_4$ receptor-modulating activity that can be incorporated into pharmaceutical compositions useful for therapeutic methods.

SUMMARY OF THE INVENTION

The invention is directed to amino heterocyclic linked pyrimidine derivatives, as well as compositions comprising and methods of using the same. Compounds of the invention have the formula (I):

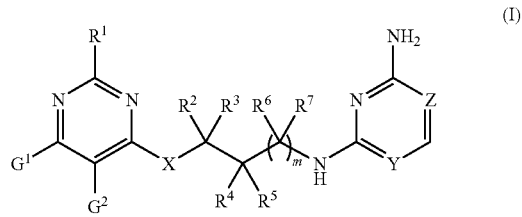

or a pharmaceutically acceptable salt, ester, amide or prodrug thereof, wherein:

X is NH, $NCH_3$, or O;

Y is N or $CR^8$;

Z is N or $CR^9$;

$R^1$ is selected from hydrogen, $NH_2$, alkyl, or fluoroalkyl;

$R^2$, $R^3$, $R^4$, $R^5$, $R^6$, and $R^7$ are each independently selected from the group consisting of hydrogen, alkoxycarbonyl, alkyl, alkylcycloalkyl, carboxy, cyano, cyanoalkyl, cycloalkoxyalkyl, cycloalkyl, fluoroalkoxy, fluoroalkyl, fluorocycloalkyl, fluorocycloalkylalkyl, fluorine, formyl, haloalkoxy, hydroxyalkyl, and $C(O)NR^{10}R^{11}$; or $R^2$ and $R^3$, or $R^4$ and $R^5$, or $R^6$ and $R^7$ taken together are —$CH_2CH_2CH_2$—, —$CH_2CH_2CH_2CH_2$—, —$CH_2CH_2CH_2CH_2CH_2$—, —$CH_2CH_2OCH_2CH_2$—, —$CH_2OCH_2CH_2$—, or —$OCH_2CH_2CH_2$—; or $R^3$ and $R^4$, or $R^5$ and $R^6$ taken together are —$CH_2CH_2CH_2$—, —$CH_2CH_2$ $CH_2CH_2$—, or —$CH_2OCH_2$—;

$R^8$ and $R^9$ are each independently selected from the group consisting of hydrogen, fluoroalkyl, and halogen;

$R^{10}$ and $R^{11}$ are each independently selected from the group consisting of hydrogen and alkyl;

$G^1$ is selected from the group consisting of hydrogen, alkyl, alkynyl, amido, aryl, arylalkenyl, arylalkyl, cycloalkyl, heteroaryl, heterocycle, and $NR^{12}R^{13}$;

$G^2$ is selected from the group consisting of hydrogen, alkyl, and arylalkyl; or, $G^1$ and $G^2$ can be taken together to form groups of formula (ii), formula (iii) or formula (iv)

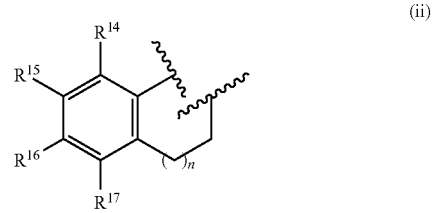

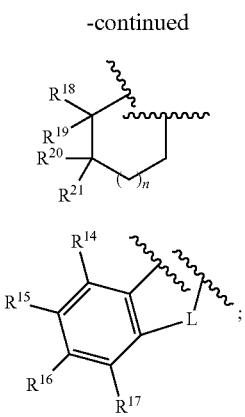

L is selected from O, S, NH, or N—CH$_3$;

R$^{12}$ and R$^{13}$ are each independently selected from the group consisting of hydrogen, alkyl, aryl, and arylalkyl;

R$^{14}$, R$^{15}$, R$^{16}$, and R$^{17}$ are each independently selected from the group consisting of hydrogen, acyl, acyloxy, alkenyl, alkoxy, alkoxyalkoxy, alkoxyalkyl, alkoxycarbonyl, alkoxyimino, alkoxysulfonyl, alkyl, alkylcycloalkyl, alkylsulfonyl, alkylthio, alkynyl, amido, aryl, halogen, fluoroalkyl, carboxy, cyano, cyanoalkyl, cycloalkoxyalkyl, cycloalkyl, fluoroalkoxy, fluorocycloalkyl, fluorocycloalkylalkyl, formyl, haloalkoxy, haloalkyl, heteroaryl, heterocycle, hydroxy, hydroxyalkyl, mercapto, nitro, C(O)NR$^{25}$R$^{26}$, NR$^{25}$C(O)alkyl, —NR$^{26}$C(O)Oalkyl, N(R$^{25}$)SO$_2$(R$^{26}$), —NR$^{25}$R$^{26}$, O-aryl, O-heteroaryl, S-aryl, and —SO$_2$(NR$^{25}$R$^{26}$); or R$^{15}$ and R$^{16}$ taken together are —CH$_2$CH$_2$CH$_2$—, —CH$_2$CH$_2$CH$_2$CH$_2$—, —CH$_2$OCH$_2$—, or —OCH$_2$CH$_2$O—;

R$^{18}$, R$^{19}$, R$^{20}$, and R$^{21}$ are each independently selected from the group consisting of hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylcycloalkyl, alkylsulfonyl, alkylthio, alkynyl, amido, aryl, carboxy, cyano, cyanoalkyl, cycloalkoxyalkyl, cycloalkyl, fluorine, fluoroalkoxy, fluoroalkyl, fluorocycloalkyl, fluorocycloalkylalkyl, fluoroalkyl, formyl, heteroaryl, heterocycle, hydroxy, hydroxyalkyl, mercapto, nitro, C(O)NR$^{25}$R$^{26}$, —NR$^{25}$C(O)alkyl, —NR$^{25}$C(O)Oalkyl, —N(R$^{25}$)SO$_2$(R$^{26}$), —NR$^{25}$R$^{26}$, O-aryl, O-heteroaryl, S-aryl, and —SO$_2$(NR$^{25}$R$^{26}$); or R$^{18}$ and R$^{19}$ taken together are —CH$_2$CH$_2$CH$_2$—, —CH$_2$CH$_2$CH$_2$CH$_2$—, —CH$_2$CH$_2$CH$_2$CH$_2$—, —CH$_2$OCH$_2$—, or —OCH$_2$CH$_2$O—; or R$^{18}$ and R$^{20}$ taken together are —CH$_2$CH$_2$CH$_2$—, —CH$_2$CH$_2$CH$_2$CH$_2$—, —CH$_2$OCH$_2$—, or —OCH$_2$CH$_2$O—;

R$^{25}$ and R$^{26}$ are independently selected from the group consisting of hydrogen, acyl, alkoxyalkyl, alkyl, aryl, arylalkyl, cyanoalkyl, cycloalkyl, cycloalkoxyalkyl, cycloalkylalkyl, fluoroalkyl, fluorocycloalkylalkyl, and hydroxyalkyl;

m is 0, or 1; and n is 0, 1, 2, or 3.

Another aspect of the invention relates to pharmaceutical compositions comprising compounds of the invention. Such compositions can be administered in accordance with a method of the invention, typically as part of a therapeutic regimen for treatment or prevention of conditions and disorders related to histamine H$_4$ receptor activity.

In addition, compounds of the invention can have the formula (I) and also demonstrate an ability to modulate histamine H$_4$ receptor activity. In this aspect, the invention relates to a method of modulating histamine H$_4$ receptor activity. The method is useful for treating, or preventing, conditions and disorders related to histamine H$_4$ receptor modulation in mammals. More particularly, the method is useful for treating or preventing conditions and disorders related to the immune system involving inflammatory processes, auto-immune disease, and also in nervous system activities involved in pain, such as inflammatory pain, and non-inflammatory pain, especially neuropathic pain. Accordingly, the compounds and compositions of the invention are useful as a medicament for treating or preventing histamine H$_4$ receptor modulated disease. Examples of such conditions and disorders include, but are not limited to, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, osteoarthritis pain, post-surgical pain, non-inflammatory pain, neuropathic pain, subcategories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

Another aspect of the invention relates to the use of the compounds of the invention (compounds of formula (I)) in combination with histamine H$_1$ antagonists (such as loratidine), histamine H$_2$ antagonists (such as nizatidine), histamine H$_3$ antagonists (such as ABT-239), modulators of TNF-α (such as adalimumab), anti-inflammatory corticocosteroids (such as dexamethasone), 5-lipoxygenase inhibitors (such as zileuton), leukotriene antagonists (such as zafirlukast) or LTB4 antagonists, with NSAIDS (such as ibuprofen) including, COX-2 inhibitors (such as celecoxib), with β-adrenergic receptor agonists such as salmeterol, anti-nociceptive opiate agonists (such as morphine), anti-nociceptive alpha adrenergic agonists (such as dexmedetomidine), TRPV1 antagonists, nicotinic agonists, CB-1 agonists, CB-2 agonists, P2X7 antagonists, metabotropic glutamate receptor antagonists, an anticonvulsant such as gabapentin or pregabilin, and a tricyclic antidepressant such as amitriptyline.

The compounds, compositions comprising the compounds, and methods for treating or preventing conditions and disorders by administering the compounds, are further described herein.

DETAILED DESCRIPTION OF THE INVENTION

Definition of Terms

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through a —C(=NH)— group, which also is defined as an imino group. Representative examples of alkoxyimino include, but are not limited to, (methoxy)imino, (ethoxy)imino and (tert-butoxy)imino.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylcycloalkyl" as used herein means an alkyl group, as defined herein, appended to the parent molecular moiety through a cycloalkyl group, as defined herein. Representative examples of alkylcycloalkyl include, but are not limited to, 4-ethylcyclohexyl, 3-methylcyclopentyl, 2-isopropylcyclopropyl and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —NH$_2$ group.

The term "aryl," as used herein, means phenyl, a bicyclic aryl, or a tricyclic aryl. The bicyclic aryl is naphthyl, a phenyl fused to a cycloalkyl, or a phenyl fused to a cycloalkenyl. The bicyclic aryl of the invention must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The carbon atoms of the aryl groups of this invention are substituted with hydrogen or are optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —NR$^{25}$R$^{26}$, ($NR^{25}R^{26}$)carbonyl, —$SO_2NR^{25}R^{26}$, —$NR^{25}C(O)NR^{25}R^{26}$, —$NR^{25}C(O)Oalkyl$, and —$N(R^{25})SO_2(R^{26})$. Where the aryl group is a phenyl group, the number of substituents is 0, 1, 2, 3, 4, or 5. Where the aryl group is a bicyclic aryl, the number of substituents is 0, 1, 2, 3, 4, 5, 6, or 7. Where the aryl group is a tricyclic aryl, the number of substituents is 0, 1, 2, 3, 4, 5, 6, 7, 8, or 9.

The term "arylalkenyl" as used herein, means an aryl group, as defined herein, appended to the parent molecular moiety through an alkenyl group, as defined herein.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "benzyl" as used herein means a phenyl group connected through methylene to the parent moiety. The phenyl portion of benzyl groups may be optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, cyano, cycloalkyl, fluoroalkoxy, haloalkoxy, haloalkyl, halogen, hydroxy, hydroxyalkyl, —$NR^{25}R^{26}$, ($NR^{25}R^{26}$)carbonyl, —$SO_2NR^{25}R^{26}$, —$NR^{25}C(O)NR^{25}R^{26}$, —$NR^{25}C(O)Oalkyl$, and —$N(R^{25})SO_2(R^{26})$.

The term "carbonyl" as used herein means a —C(═O)— group.

The term "carboxy" as used herein means a —$CO_2H$ group.

The term "cyano" as used herein means a —CN group, attached to the parent molecular moiety through the carbon.

The term "cyanoalkyl" as used herein means a —CN group attached to an alkylene, appended to the parent molecular moiety through the alkylene group. Representative examples of "cyanoalkyl" include, but are not limited to, 3-cyanopropyl, and 4-cyanobutyl.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 10 carbons. Examples of cycloalkyl include cyclopropyl, cyclobutyl, cyclopentyl, cyclohexyl, cycloheptyl, and cyclooctyl. $C_3$-$C_5$ cycloalkyl in particular refers to a saturated cyclic hydrocarbon group containing from 3 to 5 carbons, for example, cyclopropyl, cyclobutyl, and cyclopentyl.

The term "cycloalkenyl" as used herein means a cyclic hydrocarbon group containing from 3 to 10 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

Each of the carbon atoms of the cycloalkyl or cycloalkenyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, oxo, nitro, alkylthio, —$NR^{25}R^{26}$, ($NR^{25}R^{26}$)carbonyl, —$SO_2N(R^{25})(R^{26})$, —$NR^{25}C(O)NR^{25}R^{26}$, —$NR^{25}C(O)Oalkyl$, and —$N(R^{25})SO_2(R^{26})$, wherein, $R^{25}$ and $R^{26}$ are defined herein.

The term "cycloalkoxyalkyl" as used herein means a cycloalkyl group, as defined herein, appended to the parent molecular moiety through an —O-alkyl-group, wherein alkyl is as defined herein. Representative examples of cycloalkoxyalkyl include, but are not limited to, cyclobutoxymethyl, cyclopentyloxymethyl, 2-(cyclopentyloxy)ethyl and cyclohexyloxymethyl.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "cycloalkylalkyl" as used herein means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl. ($C_3$-$C_5$ cycloalkyl)alkyl in particular refers to a saturated cyclic hydrocarbon group containing from 3 to 5 carbons, for example, cyclopropyl, cyclobutyl, and cyclopentyl, appended to the parent molecular moiety through a alkyl group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" or "fluorine" as used herein means —F.

The term "fluoroalkyl" as used herein means at least one fluoro group, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, and 2,2,2-trifluoroethoxy.

The term "fluorocycloalkyl" as used herein means a fluoro as defined herein, attached to a cycloalkyl moiety, attached to the parent molecular moiety through the cycloalkyl group. Representative examples of fluorocycloalkyl include, but are not limited to, 4-fluorocyclohexyl, 2,2-difluorocyclobutyl and the like.

The term "fluorocycloalkylalkyl" as used herein means a fluorocycloalkyl group as defined herein, attached to the parent molecular moiety through the alkyl group. Representative examples of fluorocycloalkylalkyl include, but are not limited to, (4-fluorocyclohexyl)methyl, (2,2-difluorocyclobutyl)methyl and the like.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, refers to an aromatic ring containing one or more heteroatoms independently selected from nitrogen, oxygen, and sulfur. Such rings can be monocyclic or bicyclic as further described herein.

The terms "monocyclic heteroaryl" or "5- or 6-membered heteroaryl ring", as used herein, refer to 5- or 6-membered aromatic rings containing at least one heteroatom independently selected from nitrogen, oxygen, and sulfur. The 5-membered ring contains two double bonds; such a ring may contain one, two, three or four nitrogen atoms, or may contain one or two nitrogen atoms and one oxygen atom, or may contain one or two nitrogen atoms and one sulfur atom, or may contain one oxygen atom, or may contain one sulfur atom. The 6-membered ring contains three double bonds, or alternatively, the 6-membered ring may contains 2 double bonds within the ring when the ring is substituted with an oxo group. Furthermore, the 6-membered ring may contain one, two, three or four nitrogen atoms, or may contain one or two nitrogen atoms and one oxygen atom, or may contain one or two nitrogen atoms and one sulfur atom, or may contain one or two nitrogen atoms and one sulfur atom, or may contain one or two nitrogen atoms and or one oxygen atom. The 5- or 6-membered heteroaryl is connected to the parent molecular moiety through any carbon atom or any nitrogen atom contained within the monocyclic heteroaryl ring. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring wherein one or more of the atoms of the ring has been replaced with at least one heteroatom selected from oxygen, sulfur, and nitrogen. The bicyclic heteroaryl of the invention maybe attached to the parent molecular moiety through any available carbon atom or nitrogen atom contained within the heteroaryl ring. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, are substituted with hydrogen, or optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, oxo, —$NR^{25}R^{26}$, ($NR^{25}R^{26}$)carbonyl, —$SO_2N(R^{25})(R^{26})$, —$NR^{25}C(O)NR^{25}R^{26}$, —$NR^{25}C(O)$Alkyl, and —$N(R^{25})SO_2(R^{26})$. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the invention may be present as tautomers.

The term "heterocycle" or "heterocyclic" as used herein, means a monocyclic heterocycle or a bicyclic heterocycle. The monocyclic heterocycle is a 3-, 4-, 5-, 6- or 7-membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring may contain zero, one, or two double bonds provided that the ring, when taken together with a substituent, does not tautomerize with a substituent to form an aromatic ring. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, oxo, —$NR^{25}R^{26}$, ($NR^{25}R^{26}$)carbonyl, —$SO_2N(R^{25})(R^{26})$, —$NR^{25}C(O)NR^{25}R^{26}$, —$NR^{25}C(O)$Alkyl, and —$N(R^{25})SO_2(R^{26})$.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyl iodide, benzyl iodide, triethylsilyltriflate, acetyl chloride, benzyl chloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "lower alkyl" as used herein, is a subset of alkyl as defined herein and means a straight or branched chain hydrocarbon group containing from 1 to 4 carbon atoms. Examples of lower alkyl are methyl, ethyl, n-propyl, iso-propyl, n-butyl, iso-butyl, sec-butyl, and tert-butyl.

The term "lower fluoroalkyl" as used herein, is a subset of fluoroalkyl, as defined herein, and means a straight or branched chain fluoroalkyl group containing from 1 to 4 carbon atoms. Representative examples of lower fluoroalkyl include, but are not limited to, trifluoromethyl, difluoromethyl, and 1,2-difluoroethyl.

The term "mercapto" as used herein means a —SH group.

The term "($NR^{25}R^{26}$)" as used herein means both an $R^{25}$ and $R^{26}$ group, wherein $R^{25}$ and $R^{26}$ are each as defined for compounds of formula (I), are appended to the parent molecular moiety through a nitrogen atom. The "($NR^{25}R^{26}$)" is appended to the parent molecular moiety through the nitrogen.

The term "($NR^{25}R^{26}$)alkyl" as used herein means an —$NR^{25}R^{26}$ group, as defined herein, appended to the parent molecular moiety through an alkylene group, as defined herein. Representative examples of ($NR^{25}R^{26}$)alkyl include, but are not limited to, 2-(methylamino)ethyl, 2-(dimethylamino)ethyl, 2-(amino)ethyl, 2-(ethylmethylamino)ethyl, and the like.

The term "($NR^{25}R^{26}$)carbonyl" as used herein means an —$NR^{25}R^{26}$ group, as defined herein, appended to the parent molecular moiety through a carbonyl group, as defined herein. Representative examples of ($NR^{25}R^{26}$)carbonyl include, but are not limited to, aminocarbonyl, (methylamino)carbonyl, (dimethylamino)carbonyl, (ethylmethylamino)carbonyl, and the like.

The term "—$NR^{25}C(O)Oalkyl$" as used herein means an amino group attached to the parent moiety to which is further appended a $R^{25}$ group as defined herein, and a C(O), i.e. carbonyl, group to which is appended an Oalkyl, i.e. alkoxy, group. Representative examples of —$NR^{25}C(O)Oalkyl$ include, but are not limited to, methyl N-methylcarbamate, tert-butyl N-methylcarbamate, and the like.

The term "—$NR^{25}C(O)NR^{25}R^{26}$" as used herein means an amino group attached to the parent moiety to which is further appended a $R^{25}$ group as defined herein, and a $C(O)NR^{25}R^{26}$, i.e. ($NR^{25}R^{26}$)carbonyl, as defined herein. Representative examples of —$NR^{25}C(O)NR^{25}R^{26}$ include, but are not limited to, methylurea, phenyl urea, and the like.

The term "($NR^{25}R^{26}$)sulfonyl" as used herein means a —$NR^{25}R^{26}$ group, as defined herein, appended to the parent molecular moiety through a sulfonyl group, as defined herein. Representative examples of ($NR^{25}R^{26}$)sulfonyl include, but are not limited to, aminosulfonyl, (methylamino)sulfonyl, (dimethylamino)sulfonyl and (ethylmethylamino)sulfonyl.

The term "—$N(R^{25})SO_2(R^{26})$" as used herein means an amino group attached to the parent moiety to which is further appended with a $R^{25}$ group as defined herein, and a $SO_2$ group to which is appended an ($R^{26}$) group as defined herein. Representative examples of —$N(R^{25})SO_2(R^{26})$ include, but are not limited to, N-methylmethanesulfonamide.

The term "—$SO_2(NR^{25}R^{26})$" as used herein means a $NR^{25}R^{26}$ group attached to a $SO_2$ group, appended to the parent moiety through the sulfonyl group. Representative examples of —$SO_2(NR^{25}R^{26})$ include, but are not limited to (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-C=O)$_2$O, a diaryl anhydride, for example as represented by (aryl-C=O)$_2$O, an acyl halide, an alkylchloroformate, or an alkylsulfonylhalide, an arylsulfonylhalide, or halo-C(O)N(alkyl)$_2$, for example acetyl chloride, benzoyl chloride, benzyl bromide, benzyloxycarbonyl chloride, formylfluoride, phenylsulfonyl chloride, pivaloyl chloride, (tert-butyl-O—C=O)$_2$O, trifluoroacetic anhydride, and triphenylmethylchloride.

The term "oxo" as used herein means (=O).

The term "sulfonyl" as used herein means a —$S(O)_2$— group.

Antagonists are ligands that block receptor activation by an agonist. In the case of the histamine $H_4$ receptor, a histamine $H_4$ receptor antagonist blocks activation of the histamine $H_4$ receptor by a histamine $H_4$ receptor agonist such as the endogenous agonist ligand histamine. Inverse agonists are ligands that block receptor activation more generally: they block intrinsic activation of a receptor that occurs in the absence of an agonist activation by an agonist, and also block receptor activation by an agonist. Partial agonists are ligands that bind to receptors but only partially activate the receptor; in so doing, partial agonists compete with full agonists and block full activation of the receptor. In the case of the histamine $H_4$ receptor, the endogenous agonist histamine is a full agonist.

Compounds of the Invention

Compounds of the invention can have the formula (I) as described in the Summary of the Invention. In addition, certain embodiments of the invention further describe compounds of formula (I):

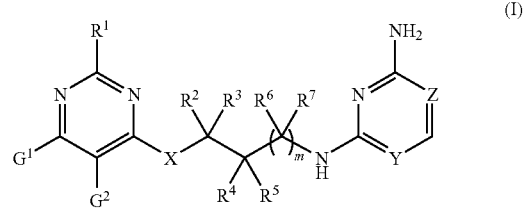

In a compound of formula (I), X is NH, NCH$_3$, or O. Preferably, X is NH or NCH$_3$.

m is 0 or 1.

Y is N or CR$^8$. Preferably, Y is CR$^8$.

Z is N or CR$^9$. Preferably, Z is N.

R$^1$ is selected from hydrogen, NH$_2$, alkyl, or fluoroalkyl. Preferably, R$^1$ is NH$_2$.

$R^2$, $R^3$, $R^4$, $R^5$, $R^6$, and $R^7$ are each independently selected from the group consisting of hydrogen, alkoxycarbonyl, alkyl, alkylcycloalkyl, carboxy, cyano, cyanoalkyl, cycloalkoxyalkyl, cycloalkyl, fluoroalkoxy, fluoroalkyl, fluorocycloalkyl, fluorocycloalkylalkyl, fluorine, formyl, haloalkoxy, hydroxyalkyl, and $C(O)NR^{10}R^{11}$. Preferably, $R^2$, $R^3$, $R^4$, $R^5$, $R^6$, and $R^7$ are hydrogen.

In another embodiment, $R^2$ and $R^3$, or $R^4$ and $R^5$, or $R^6$ and $R^7$ taken together are —$CH_2CH_2CH_2$—, —$CH_2CH_2CH_2CH_2$—, —$CH_2CH_2CH_2CH_2CH_2$—, —$CH_2CH_2OCH_2CH_2$—, —$CH_2OCH_2CH_2$—, or —$OCH_2CH_2CH_2$— forming a spirocyclic ring.

In yet another embodiment, $R^3$ and $R^4$, or $R^5$ and $R^6$ taken together are —$CH_2CH_2CH_2$—, —$CH_2CH_2CH_2CH_2$—, or —$CH_2OCH_2$— forming either a 5- or 6-membered ring.

$R^8$ and $R^9$ are each independently selected from the group consisting of hydrogen, fluoroalkyl, and halogen.

$R^{10}$ and $R^{11}$ are each independently selected from the group consisting of hydrogen and alkyl.

$G^1$ is selected from the group consisting of hydrogen, alkyl, alkynyl, amido, aryl, arylalkenyl, arylalkyl, cycloalkyl, heteroaryl, heterocycle, and $NR^{12}R^{13}$ wherein $R^{12}$ and $R^{13}$ are each independently selected from the group consisting of hydrogen, alkyl, aryl, and arylalkyl. Preferably, $G^1$ is alkyl, amido, aryl, arylalkenyl or $NR^{12}R^{13}$, wherein $R^{12}$ and $R^{13}$ is selected from hydrogen, alkyl, aryl, and arylalkyl. In a more preferred embodiment, $G^1$ is phenyl or m-chlorophenyl.

$G^2$ is selected from hydrogen, alkyl, or arylalkyl.

Alternatively, $G^1$ and $G^2$ can be taken together to form groups of formula (ii), formula (iii) or formula (iv)

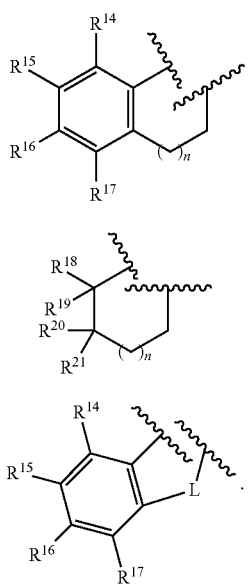

L is selected from O, S, NH, or N—$CH_3$. n is selected from 0, 1, 2, or 3.

For compounds of formula (ii), n is preferably 1 or 2.
For compounds of formula (iii), n is preferably 1 or 2.
For compounds of formula (iv), preferably L is O.

$R^{14}$, $R^{15}$, $R^{16}$, and $R^{17}$ are each independently selected from the group consisting of hydrogen, acyl, acyloxy, alkenyl, alkoxy, alkoxyalkoxy, alkoxyalkyl, alkoxycarbonyl, alkoxyimino, alkoxysulfonyl, alkyl, alkylcycloalkyl, alkylsulfonyl, alkylthio, alkynyl, amido, aryl, halogen, fluoroalkyl, carboxy, cyano, cyanoalkyl, cycloalkoxyalkyl, cycloalkyl, fluoroalkoxy, fluorocycloalkyl, fluorocycloalkylalkyl, formyl, haloalkoxy, haloalkyl, heteroaryl, heterocycle, hydroxy, hydroxyalkyl, mercapto, nitro, $C(O)NR^{25}R^{26}$, —$NR^{25}C(O)$alkyl, —$NR^{26}C(O)O$alkyl, $N(R^{25})SO_2(R^{26})$, —$NR^{25}R^{26}$, O-aryl, O-heteroaryl, S-aryl, and —$SO_2(NR^{25}R^{26})$. In one embodiment, $R^{15}$ in a group of formula (iv) is hydrogen or halogen.

In one embodiment, $R^{15}$ and $R^{16}$ taken together are —$CH_2CH_2CH_2$—, —$CH_2CH_2CH_2CH_2$—, —$CH_2OCH_2$—, or —$OCH_2CH_2O$— forming a 5- or 6-membered ring.

$R^{18}$, $R^{19}$, $R^{20}$, and $R^{21}$ are each independently selected from the group consisting of hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylcycloalkyl, alkylsulfonyl, alkylthio, alkynyl, amido, aryl, carboxy, cyano, cyanoalkyl, cycloalkoxyalkyl, cycloalkyl, fluorine, fluoroalkoxy, fluoroalkyl, fluorocycloalkyl, fluorocycloalkylalkyl, fluoroalkyl, formyl, heteroaryl, heterocycle, hydroxy, hydroxyalkyl, mercapto, nitro, $C(O)NR^{25}R^{26}$, —$NR^{25}C(O)$alkyl, —$NR^{25}C(O)O$alkyl, $N(R^{25})SO_2(R^{26})$, —$NR^{25}R^{26}$, O-aryl, O-heteroaryl, S-aryl, and —$SO_2(NR^{25}R^{26})$. In one preferred embodiment for compounds of formula (iii) $R^{18}$ is aryl. In another preferred embodiment for compounds of formula (iii), $R^{20}$ is aryl.

Alternatively, in compounds of formula (iii), $R^{18}$ and $R^{19}$ taken together are —$CH_2CH_2CH_2$—, —$CH_2CH_2CH_2CH_2$—, —$CH_2CH_2CH_2CH_2CH_2$—, —$CH_2OCH_2$—, or —$OCH_2CH_2O$— forming a spirocyclic 4-, 5-, or 6-membered ring. Preferably, $R^{18}$ and $R^{19}$ taken together are —$CH_2CH_2CH_2$— or —$CH_2CH_2CH_2CH_2CH_2$—.

In another embodiment, $R^{18}$ and $R^{20}$ taken together are —$CH_2CH_2CH_2$—, —$CH_2CH_2CH_2CH_2$—, —$CH_2OCH_2$—, or —$OCH_2CH_2O$— and form a 5- or 6-membered ring.

$R^{25}$ and $R^{26}$ are independently selected from the group consisting of hydrogen, acyl, alkoxyalkyl, alkyl, aryl, arylalkyl, cyanoalkyl, cycloalkyl, cycloalkoxyalkyl, cycloalkylalkyl, fluoroalkyl, fluorocycloalkylalkyl, and hydroxyalkyl.

m is 0, or 1.

In one embodiment, $R^1$ is $NH_2$; $R^2$, $R^3$, $R^4$, $R^5$, $R^6$, $R^7$ $R^8$, $R^{14}$, $R^{15}$, $R^{16}$ and $R^{17}$ when present are hydrogen; X is NH or $NCH_3$; Y is $CR^8$; Z is N; m is 0 or 1; n is 2, and $G^1$ and $G^2$ taken together are a group of formula (ii).

In another embodiment, $R^1$ is $NH_2$; $R^2$, $R^3$, $R^4$, $R^5$, $R^9$, $R^{14}$, $R^{15}$, $R^{16}$ and $R^{17}$ are hydrogen; X is NH; Y is N; Z is $CR^9$; m is 0; n is 2, and $G^1$ and $G^2$ taken together are a group of formula (ii).

In a further embodiment, $R^1$ is $NH_2$; $R^2$, $R^3$, $R^4$, $R^5$, and $R^8$ are hydrogen; X is NH; Y is $CR^8$; Z is N; m is 0; $G^1$ is aryl; and $G^2$ is hydrogen.

In another embodiment, $R^1$ is $NH_2$; $R^2$, $R^3$, $R^4$, $R^5$, and $R^8$ are hydrogen; X is NH; Y is $CR^8$; Z is N; m is 0; $G^1$ is arylalkenyl; and $G^2$ is hydrogen.

In a further embodiment, $R^1$ is $NH_2$; $R^2$, $R^3$, $R^4$, $R^5$, and $R^8$ are hydrogen; X is NH; Y is $CR^8$; Z is N; m is 0; and $G^1$ and $G^2$ taken together are a group of formula (iii) wherein $R^{18}$ and $R^{19}$ taken together are —$CH_2CH_2CH_2CH_2$—.

In another embodiment, $R^1$ is $NH_2$; $R^2$, $R^3$, $R^4$, $R^5$, and $R^8$ are hydrogen; X is NH; Y is $CR^8$; Z is N; m is 0; and $G^1$ and $G^2$ taken together are a group of formula (iii) wherein $R^{21}$ is aryl.

In another embodiment, $R^1$, $R^2$, $R^3$, $R^4$, $R^5$, and $R^8$ are hydrogen; X is NH; Y is $CR^8$; Z is N; m is 0; and $G^1$ and $G^2$ taken together are a group of formula (iv) wherein L is O.

Suitable groups for $G_1$, $G_2$, m, n, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{25}$, $R^{26}$, X, Y and Z in compounds of formula (I) are each independently selected. The described embodiments of the present invention may be combined. Such combination is contemplated and within the scope of the present invention. For example, it is contemplated that preferred groups for any of $G_1, G_2$, m, n, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{25}, R^{26}$, X, Y and Z can be combined with groups defined for any other of $G_1, G_2$, m, n, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{25}, R^{26}$, X, Y and Z whether or not such group is preferred.

There also exist a pharmaceutical composition comprising a compound of formula (I) and a pharmaceutically acceptable carrier.

Exemplary compounds of various embodiments of the invention include, but are not limited to:

$N^4$-{2-[(2-aminopyrimidin-4-yl)amino]ethyl}-6,7-dihydro-5H-benzo[6,7]cyclohepta[1,2-d]pyrimidine-2,4-diamine;

$N^4$-{2-[(2-aminopyrimidin-4-yl)amino]ethyl}-$N^4$-methyl-6,7-dihydro-5H-benzo[6,7]cyclohepta[1,2-d]pyrimidine-2,4-diamine;

$N^4$-{3-[(2-aminopyrimidin-4-yl)amino]propyl}-6,7-dihydro-5H-benzo[6,7]cyclohepta[1,2-d]pyrimidine-2,4-diamine;

$N^4$-{2-[(4-aminopyrimidin-2-yl)amino]ethyl}-6,7-dihydro-5H-benzo[6,7]cyclohepta[1,2-d]pyrimidine-2,4-diamine;

$N^4$-{2-[(2-aminopyrimidin-4-yl)amino]ethyl}-6-phenylpyrimidine-2,4-diamine;

$N^4$-{2-[(2-aminopyrimidin-4-yl)amino]ethyl}-6-(3-chlorophenyl)pyrimidine-2,4-diamine;

$N^4$-{2-[(2-aminopyrimidin-4-yl)amino]ethyl}-6-(3,5-dichlorophenyl)pyrimidine-2,4-diamine;

$N^4$-{2-[(2-aminopyrimidin-4-yl)amino]ethyl}-6-(5-chloro-2-methoxyphenyl)pyrimidine-2,4-diamine;

$N^4$-{2-[(2-aminopyrimidin-4-yl)amino]ethyl}-6-[(E)-2-phenylvinyl]pyrimidine-2,4-diamine;

$N^{4'}$-{2-[(2-aminopyrimidin-4-yl)amino]ethyl}-6',7'-dihydro-5'H-spiro[cyclopentane-1,8'-quinazoline]-2',4'-diamine;

$N^4$-{2-[(2-aminopyrimidin-4-yl)amino]ethyl}-8-phenyl-6,7,8,9-tetrahydro-5H-cyclohepta[d]pyrimidine-2,4-diamine; or $N^4$-[2-([1]benzofuro[3,2-d]pyrimidin-4-ylamino)ethyl]pyrimidine-2,4-diamine.

The practice of assigning names to chemical compounds from structures, and of assigning chemical structures from given chemical names is well known to those of ordinary skill in the art.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes and cyclohexanes may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen, deuterium and tritium, or $^{12}C$, $^{11}C$ and $^{13}C$, or $^{19}F$ and $^{18}F$.

Methods of the Invention

Compounds and compositions of the invention are useful for modulating the histamine $H_4$ receptor, particularly by histamine $H_4$ receptor antagonism, partial agonism, or inverse agonism. In particular, the compounds and compositions of the invention can be used for treating and preventing disorders modulated by the histamine $H_4$ receptor. Typically, such disorders can be ameliorated by modulating histamine $H_4$ receptors in a mammal, preferably by administering a compound or composition of the invention, either alone or in combination with another active agent, for example, as part of a therapeutic regimen.

Certain substituted amino heterocyclic linked pyrimidine compounds, including but not limited to those specified as compounds of the invention, demonstrate the ability to affect histamine $H_4$ receptor activity, and in particular demonstrate histamine $H_4$ receptor antagonism. Such compounds can be useful for the treatment and prevention of a number of histamine $H_4$ receptor-mediated diseases or conditions. Compounds of the invention demonstrate such activity and have the formula (I), as previously defined herein.

There is also disclosed a method of treating a mammal having a condition where modulation of histamine $H_4$ receptor activity is of therapeutic benefit, said method comprising administering to a subject having or susceptible to said disorder with a therapeutically effective amount of a compound of the formula (I), or a pharmaceutically acceptable salt, ester, amide, or prodrug thereof, as presented in the Summary of the Invention and Detailed Description of the Invention herein.

There is also disclosed a method of treating a mammal having a condition where modulation of histamine $H_4$ receptor activity is of therapeutic benefit. The method comprises administering to a subject having or susceptible to said disorder a therapeutically effective amount of a compound of the formula (I), as previously defined.

The method is particularly beneficial when the condition or disorder is asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, autoimmune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, or spinal cord injury pain.

In particular, it is particularly beneficial to administer compounds of formula (I) for the prevention and treatment of asthma.

It also is particularly beneficial to administer compounds of formula (I) for the prevention and treatment of inflammation.

It also is particularly beneficial to administer compounds of formula (I) for the prevention and treatment of pain. More particularly, it is beneficial to administer compounds of formula (I) for prevention and treatment of inflammatory pain. Compounds of formula (I) also demonstrate therapeutic benefit in treating and preventing non-inflammatory pain. In particular, compounds of formula (I) can be administered for treatment and prevention of neuropathic pain.

As an important consequence of the ability of the compounds of the invention to modulate the effects of histamine $H_4$ receptors in cells, the compounds described for the method of the invention can affect physiological processes in humans and animals. In this way, the compounds and compositions of formula (I) are useful for treating and preventing diseases and disorders modulated by histamine $H_4$ receptors. Typically, treatment or prevention of such diseases and disorders can be effected by modulating the histamine $H_4$ receptors in a mammal, by administering a compound or composition of the invention, either alone or in combination with another active agent as part of a therapeutic regimen.

Particularly preferred are compounds of formula (I) for the method, include, but are not limited to, $N^4$-{2-[(2-aminopyrimidin-4-yl)amino]ethyl}-$N^4$-methyl-6,7-dihydro-5H-benzo[6,7]cyclohepta[1,2-d]pyrimidine-2,4-diamine, $N^4$-{2-[(2-aminopyrimidin-4-yl)amino]ethyl}-6-phenylpyrimidine-2,4-diamine, $N^4$-{2-[(2-aminopyrimidin-4-yl)amino]ethyl}-6-(3-chlorophenyl)pyrimidine-2,4-diamine, and $N^{4'}$-{2-[(2-aminopyrimidin-4-yl)amino]ethyl}-6',7'-dihydro-5'H-spiro[cyclopentane-1,8'-quinazoline]-2',4'-diamine.

Compounds of formula (I) can be administered to a subject having such a disorder or susceptible to such disorders in a therapeutically effective amount. The compounds are particularly useful for a method of treating a mammal having a condition where modulation of histamine $H_4$ receptor activity is of therapeutic benefit, wherein the method is accomplished by administering a therapeutically effective amount of a compound of formula (I) to a subject having, or susceptible to, such a disorder.

Compounds useful for the method of the invention include but are not limited to those specified in the examples, and possess an affinity for the histamine $H_4$ receptor. Such compounds therefore may be useful for the treatment and prevention of diseases or conditions related to histamine $H_4$ modulation. Examples of such diseases or conditions are, for example, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, autoimmune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain. The ability of histamine $H_4$ receptor modulators, and consequently the compounds of the invention, to prevent or treat such disorders is demonstrated by evidence and examples found in references which follow.

Histamine $H_4$ receptor ligands have utility in treatment of a number of diseases and conditions, including asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

The histamine $H_4$ receptor, or gene message coding for the histamine $H_4$ receptor (detected as cDNA by reverse transcriptase polymerase chain amplification (RTPCR) of cellular messenger (mRNA)), has been detected in a number of cells and tissues critically affected in disease conditions. For example, the histamine $H_4$ receptor plays a critical role in inflammation, in autoimmune disorders such as rheumatoid arthritis, and in disorders of the immune system. For example, the histamine $H_4$ receptor has been detected in cells of the immune system and in organs of the immune system: neutrophils, eosinophils, basophils, dendritic cells, mast cells, bone marrow, thymus, spleen, brain. For examples, see Liu, et al. Molecular Pharmacology (2001) vol. 59 pp. 420-426; de Esch, et al. Trends in Pharmacological Sciences vol. 26 No. 9 pp. 462-469; Oda, et al. Journal of the Pharmacological Society (2005) vol. 98, pp. 319-322; Zhu, et al. Molecular Pharmacology, (2001), v. 59, pp. 434-441; Gutzmer, et al. Journal of Immunology (2005) vol. 174 pp. 5224-5232; Coge, et al., Biochemical and Biophysical Research Communications (2001) vol. 284, pp. 301-309.

The histamine $H_4$ receptor is found at high (compared to normal) levels in disease tissues in rheumatoid arthritis, see for example, Grzybowska-Kowalczyk, et al. Inflammation Research (2007), 56, Supplement 1, S1-S2; Maslinska, et al.

34th Meeting of the European Histamine Research Society in Bled, Slovenia 2005 poster number 3; Jablonowska, et al. 35th Meeting of the European Histamine Research Society in Delphi, Greece (May 10-13, 2006) presentation O36; and Ikawa, et al. Biol. Pharm. Bull. (2005) vol. 28(10) pp. 2016-2018.

The role of histamine $H_4$ receptors in allergy, asthma, and allergic airway inflammation is shown by the finding that transgenic mice without histamine $H_4$ receptors are resistant to the development of disease in an animal model of asthma. The observation that a selective synthetic $H_4$ ligand elicits the same benefit in the asthma model also supports the benefits of $H_4$ ligands in treatment of disease. For example, see Dunford, et al. The Journal of Immunology (2006) vol. 176, pp. 7062-7070.

General reviews and papers on the role of histamine receptor in disease include Akdis and Simons European Journal of Pharmacology (2006) vol. 533 pp. 69-76; de Esch, et al. Trends in Pharmacological Sciences vol. 26 No. 9 pp. 462-469; Thurmond, et al. Journal of Pharmacology and Experimental Therapeutics (2004) vol. 309 pp. 404-413; Buckland, et al. British Journal of Pharmacology (2003) vol. 140, 1117-1127. The utility for histamine $H_4$ receptor ligands in cancer is supported by the finding that the $H_4$ receptor has been found expressed on mammary cell carcinoma tissues, as reported by Maslinska, et al. 34th Meeting of the European Histamine Research Society in Bled, Slovenia (May 11-15, 2005) presentation. Histamine $H_4$ receptor activation was found to exert a proliferative effect in cancer tissues, Cianchi, et al. Clinical Cancer Research (2005) vol. 11(19) pp. 6807-6815. In gastritis and gastric lesions, histamine $H_4$ ligands were found to reduce the lesions induced by administration of indomethacin in vivo: Coruzzi, et al. Jablonowska, et al. 35th Meeting of the European Histamine Research Society in Delphi, Greece (May 10-13, 2006) presentation O44. In colitis, histamine $H_4$ ligands were found to reduce the lesions induced by administration of trinitrobenzesulfonic acid in vivo: Varga, et al. European Journal of Pharmacology (2005) vol. 522 pp. 130-138; and Fogel, et al. 35th Meeting of the European Histamine Research Society in Delphi, Greece (May 10-13, 2006) presentation P32. In itch and pruritis, the benefit of histamine $H_4$ receptor ligands has been shown by Bell, et al. British Journal of Pharmacology (2004) vol. 142, pp. 374-380.

The invention also relates to a use of the compounds of the invention as $H_4$ receptor ligands to treat pain, including distinctly different types of pain, including inflammatory pain, chemically induced pain, pain resulting from surgery, pain resulting from burns, pain resulting from osteoarthritis, non-inflammatory pain, and neuropathic pain. Neuropathic pain is distinct from other types of pain (e.g. inflammatory pain) in that it can develop in response to previous or ongoing tissue, nerve injury, or diabetes, but it persists long after signs of the original injury or damage have disappeared. The usefulness of histamine $H_4$ receptor ligands in treating pain has been demonstrated (Coruzzi, et al, *Eur. J. Pharmacol.* 2007, 563, 240-244).

Neuropathic pain is distinct from other types of pain (e.g. inflammatory pain) in that it can develop in response to previous or ongoing tissue, nerve injury, or diabetes, but it persists long after signs of the original injury or damage have disappeared. Neuropathic pain is associated with allodynia, hyperalgesia, or causalgia (Dworkin Clinical Journal of Pain (2002) vol. 18(6) pp. 343-9). Allodynia is the perception of pain following a stimulus that would not normally be painful. Hyperalgesia is an enhanced response to a mildly noxious stimulus. Causalgia is described as a chronic burning pain that shows persistence in the absence of obvious noxious stimuli.

Neuropathic pain is not well treated with current therapies and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell, Expert Opinion on Emerging Drugs (2005) vol. 10(1), pp. 95-108; Vinik and Mehrabyan, Medical Clinics of North America (2004), vol. 88(4), pp. 947-999; Dray, Urban, and Dickenson, Trends in Pharmacological Sciences (1994) vol. 15(6) pp. 190-7; and Dworkin, Clinical Journal of Pain (2002) vol. 18(6) pp. 343-9. A number of animal models of neuropathic pain that can be used to assess the ability of the compounds of the invention to treat neuropathic pain exist and are further discussed inter alia. Representative compounds of the invention could be effective in treatment of neuropathic pain. Representative compounds of the invention could also be effective in treating other types of pain, non-inflammatory pain, post surgical pain, and inflammatory pain.

Neuropathic pain is a description that encompasses more specific names of pain that are sub-categories of neuropathic pain (Dworkin, Clinical Journal of Pain (2002) vol. 18(6) pp. 343-9) including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

In addition to neuropathic pain, there are other types of pain that are not inflammatory or not due to ongoing inflammation, including osteoarthritis pain, cancer pain, and visceral pain. A general review of animal models of pain is found in Joshi and Honore, Expert Opinion in Drug Discovery (2004) 1, pp. 323-334. Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in a pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 5 to about 500 micromoles/kg of body weight. For purposes of oral administration, more preferable doses can be in the range of from about 30 to about 500 micromoles/kg body weight. If desired, the effective daily dose can be divided into multiple doses for purposes of administration; consequently, single dose compositions may contain such amounts or submultiples thereof to make up the daily dose.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: BINAP for 2,2'-bis(diphenylphosphino)-1,1'-binaphthyl; Boc for t-butyloxycarbonyl; DMAP for 4-(dimethylamino)pyridine; DMF for N,N-dimethylformamide; DMSO for dimethyl sulfoxide; dppf for 1,1'-bis(diphenylphosphino)ferrocene; $Et_2O$ for diethyl ether; EtOAc for ethyl acetate; EtOH for ethanol; EtONa for sodium ethoxide; HPLC for high pressure liquid chromatography; IPA for isopropyl alcohol; LDA for lithium diisopropylamide; MCPBA for 3-chloroperoxybenzoic acid; Me for methyl; MeOH for methanol; Ms for methanesulfonyl; Pd for palladium; tBu for tert-butyl; TEA or $NEt_3$ for triethylamine; TFA for trifluoroacetic acid; THF for tetrahydrofuran; Tf represents trifluoromethanesulfonyl; and Ts for para-toluensulfonyl; dba for dibenzylidineacetone, Trityl for triphenylmethyl, rt for "room temperature" or ambient temperature suitably ranging 17-30° C. As identifiers of compounds available from descriptions reported in the literature or available commercially, CAS numbers may be used; CAS numbers are identifier numbers assigned to compounds by Chemical Abstracts Service of the American Chemical Society, and are well known to those of ordinary skill in the art.

The compounds of this invention can be prepared by a variety of synthetic procedures. Representative procedures are shown in, but are not limited to Schemes 1-11.

Scheme 1

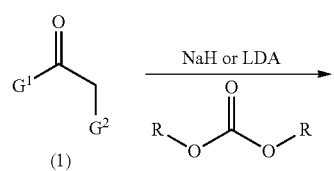

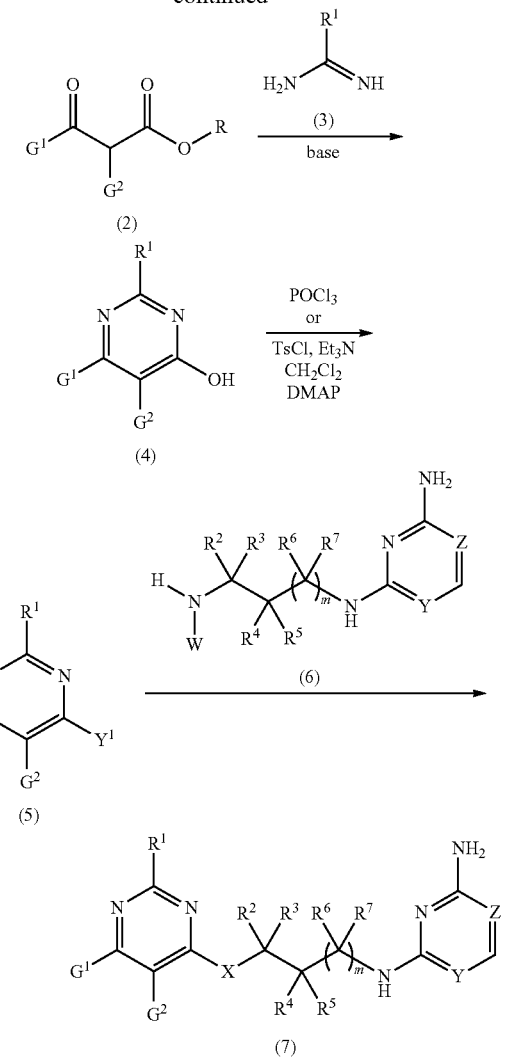

Compounds of formula (7), wherein $R^1$, $R^2$, $R^3$, $R^4$, $R^5$, $R^6$, $R^7$, m, Y, Z, $G^1$ and $G^2$ are defined in formula (I), and X is NH or $NCH_3$, may be prepared as outlined in Scheme 1. Ketones of formula (1), which are obtained either from commercial sources or synthesized through the methods outlined herein, when treated with a base such as sodium hydride or lithium diisopropylamide, followed by treatment with either a carbonate such as dimethyl carbonate, or a chloroformate such as ethyl chloroformate, will provide keto-ester containing compounds of formula (2), wherein R is lower alkyl. Compounds of formula (2) when treated with a compound of formula (3), such as guanidine nitrate, in the presence of a base such as potassium carbonate under heated conditions in a solvent such as N,N-dimethylformamide will provide compounds of formula (4). Compounds of formula (4) can exist as shown in the structure in Scheme 1 or in a tautomeric form. Compounds of formula (4) when treated with a chlorinating reagent such as but not limited to phosphorous(V) oxychloride ($POCl_3$), with or without heating as needed, will provide compounds of formula (5), wherein $Y^1$ is Cl. Alternatively, compounds of formula (4) may also be treated with reagents such as para-toluensulfonyl chloride, methylsulfonyl chloride or trifluoromethanesulfonyl chloride in the presence of a base such as triethylamine in a solvent such as pyridine or chloroform to provide compounds of formula (5) wherein $Y^1$ is $O—SO_2—R'$, wherein R' is lower alkyl, lower fluoroalkyl or aryl. Compounds of formula (5), wherein $Y^1$ is Cl or —$O—SO_2—R'$, when treated with compounds of formula (6), wherein W is H or methyl under heated conditions in the presence or absence of a base such as triethylamine or diisopropyethylamine, in a solvent such as ethanol, 2-methoxyethanol, toluene or acetonitrile, will provide compounds of formula (7).

Compounds of formula (7) wherein $R^1$ is H and $R^2$, $R^3$, $R^4$, $R^5$, $R^6$, $R^7$, m, Y, Z, $G^1$ and $G^2$ are defined in formula (1) may be prepared by treating a compound of formula (2) with thiourea with heating in the presence of a base such as sodium methoxide in a solvent such as methanol, followed by reduction of the resulting product using a reagent such as Raney® nickel to provide compounds of formula (4) wherein $R^1$ is H. Compounds of formula (4) wherein $R^1$ is H can be treated according to the methods above to provide compounds of formula (7) wherein $R^1$ is H.

Compounds of formula (7), may be further treated according to conditions known to one skilled in the art to alter functional groups contained with in the compound, for example, the removal of a protecting group such as t-butoxycarbonyl or triphenylmethyl, or hydrolysis of an ester group that will generate compounds of the present invention or used within the scope of other schemes described herein.

Compounds of formula (7) generated through the methods outlined in Scheme 1, may contain a Br, I or trifluoromethanesulfonate functional group in one of the $R^{14}$, $R^{15}$, $R^{16}$ or $R^{17}$ positions defined by $G^1$ and $G^2$ when joined together to from groups of formula (ii) or (iv) as defined for formula (I). These functional groups may be utilized as a site for introducing a carbon or nitrogen atom containing substituent at that position. Such reactions are known to one skilled in the art. For example, compounds of formula (7), containing a Br, I or trifluoromethanesulfonate functional group in one of the positions represented by $R^{14}$, $R^{15}$, $R^{16}$ or $R^{17}$ when treated with an aryl or heteroaryl boronic acids or boronic ester according to the conditions known to one skilled in the art as the Suzuki reaction will provide compounds wherein the Br, I or trifluoromethanesulfonate has been replaced by an aryl or heteroaryl group. Alternatively, using the Stille coupling reaction, compounds of formula (7) wherein one of $R^{14}$, $R^{15}$, $R^{16}$ or $R^{17}$ is Br, I or trifluoromethanesulfonate, when treated with a vinyl, aryl or heteroaryl stannane will provide compounds wherein the Br, I or trifluoromethanesulfonate has been replaced by the vinyl, aryl or heteroaryl group. Alternatively, compounds of formula (7) wherein one of $R^{14}$, $R^{15}$, $R^{16}$ or $R^{17}$ is Br, I or trifluoromethanesulfonate, when treated with amines, heterocycles or heteroaryls containing an NH group will provide compounds wherein the Br, I or trifluoromethanesulfonate has been replaced by the amine, heterocycle or heteroaryl group. Procedures and condition describing these transformations may be found in the following references: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174, (2000); F. Y. Kwong et al., Org. Lett., 4:581-584, (2002); A. Klapars et al., J. Amer. Chem. Soc., 123:7727-7729 (2001); B. H. Yang et al., J. Organomet. Chem., 576:125-146 (1999); A. Kiyomori et al., Tet. Lett., 40:2657-2640 (1999); and J. Hartwig, J. Org. Chem., 64(15):5575-5580 (1999). Alternatively, compounds of formula (7) wherein one of $R^{14}$, $R^{15}$, $R^{16}$ or $R^{17}$ is Br, I or trifluoromethanesulfonate, may be subjected to conditions commonly known as the Heck and Sonogashira reactions, to introduce an alkene or alkyne group at the site of the Br, I or trifluoromethanesulfonate moiety.

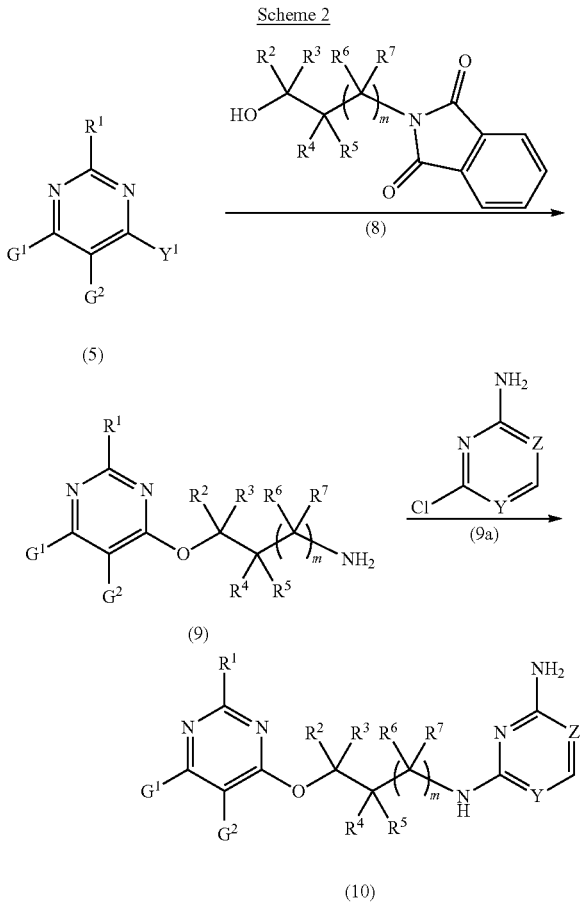

Scheme 2

Compounds of formula (10), wherein $R^1$, $R^2$, $R^3$, $R^4$, $R^5$, $R^6$, $R^7$, m, Y, Z, $G^1$ and $G^2$ are defined in formula (I), may be prepared as outlined in Scheme 2. Alcohols of formula (8), which are obtained either from commercial sources or synthesized through the methods outlined herein, can be treated with a base such as sodium hydride, then treated with compounds of formula (5), wherein $Y^1$ is Cl, and then heated to provide compounds of formula (9). Alternative bases such as potassium tert-butoxide, potassium hydride, and potassium carbonate may also be employed. More generally, alcohols of formula (8) are described in the scientific literature and may be prepared by those or ordinary skill in the art of organic synthesis.

Compounds of formula (9) can be reacted with compounds of formula (9a) to form compounds of formula (10). The reaction can optionally be heated and optionally in the presence of a base such as but not limited to diazabicyloundecane, triethylamine, potassium carbonate or sodium carbonate. Suitable solvents include but are not limited to methanol, ethanol, butanol, N,N-dimethylformamide, tetrahydrofuran, and a mixture of acetonitrile and water.

Compounds of formula (10), may be further reacted according to conditions known to those of ordinary skill in the art of organic synthesis to alter functional groups. For example, the removal of a protecting group such as t-butoxycarbonyl or hydrolysis of an ester group that will generate compounds of the present invention or be further transformed within the scope of other schemes described herein.

Compounds of formula (10) generated through the methods outlined in Scheme 2 may contain a Br, I or trifluoromethanesulfonate functional group in one of the positions represented by $R^{14}$, $R^{15}$, $R^{16}$ or $R^{17}$ as defined by $G^1$ and $G^2$. These functional groups may be utilized as a site for introducing a carbon or nitrogen atom containing substituent at that position. Such reactions are known to one skilled in the art. For example, compounds of formula (10), containing a Br, I or trifluoromethanesulfonate functional group in one of the positions represented by $R^{14}$, $R^{15}$, $R^{16}$ or $R^{17}$ when treated with an aryl or heteroaryl boronic acids or boronic esters according to the conditions known to one skilled in the art as the Suzuki reaction will provide compounds wherein the Br, I or trifluoromethanesulfonate has been replaced by an aryl or heteroaryl group. Alternatively, using the Stille coupling reaction, compounds of formula (10) wherein one of $R^{14}$, $R^{15}$, $R^{16}$ or $R^{17}$ is Br, I or trifluoromethanesulfonate, when treated with a vinyl, aryl or heteroaryl stannanes will provide compounds wherein the Br, I or trifluoromethanesulfonate has been replaced by the vinyl, aryl or heteroaryl group. Alternatively, compounds of formula (10) wherein one of $R^{14}$, $R^{15}$, $R^{16}$ or $R^{17}$ is Br, I or trifluoromethanesulfonate, when treated with amines, heterocycles or heteroaryls containing an NH group will provide compounds of wherein the Br, I or trifluoromethanesulfonate has been replaced by the amine, heterocycle or heteroaryl group. Procedures and conditions describing these transformations may be found in the following references: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174, (2000); F. Y. Kwong et al., Org. Lett., 4:581-584, (2002); A. Klapars et al., J. Amer. Chem. Soc., 123:7727-7729 (2001); B. H. Yang et al., J. Organomet. Chem., 576:125-146 (1999); A. Kiyomori et al., Tet. Lett., 40:2657-2640 (1999); and J. Hartwig, J. Org. Chem., 64(15):5575-5580 (1999). Alternatively, compounds of formula (10) wherein one of $R^{14}$, $R^{15}$, $R^{16}$ or $R^{17}$ is Br, I or trifluoromethanesulfonate, may be subjected to conditions commonly known as the Heck and Sonogashira reaction, to introduce an alkene or alkyne group at the site of the Br, I or trifluoromethanesulfonate moiety.

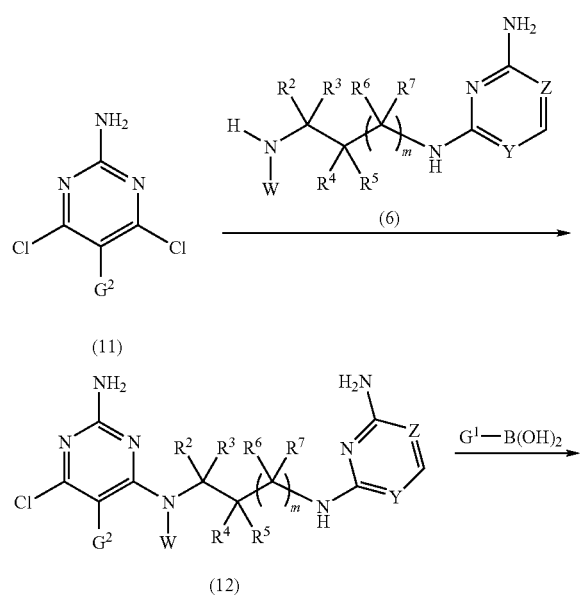

Compounds of formula (13), wherein $R^2$, $R^3$, $R^4$, $R^5$, $R^6$, $R^7$, m, Y, Z, $G^1$ and $G^2$ are defined in formula (I) may be prepared as outlined in Scheme 3. Compounds of formula (11) can be obtained from commercial sources or prepared by methods known to one skilled in the art of organic synthesis. The 4,6-dichloropyrimidine can be combined with compounds of formula (6), where W is H or methyl, as described in the above methodologies to afford compounds of formula (12). Boronic acids, commercially available or synthesized by known methods to one skilled in the art of organic synthesis and represented by $G^1$-$B(OH)_2$ wherein $G^1$ is defined in formula (I), can be coupled to (12) in the presence of a palladium catalyst such as, but not limited to, dichlorobis(triphenylphosphine)palladium(II) and a base such as, but not limited to, potassium carbonate in a solvent system such as, but not limited to, 9:1 dioxane and water to afford compounds of formula (13).

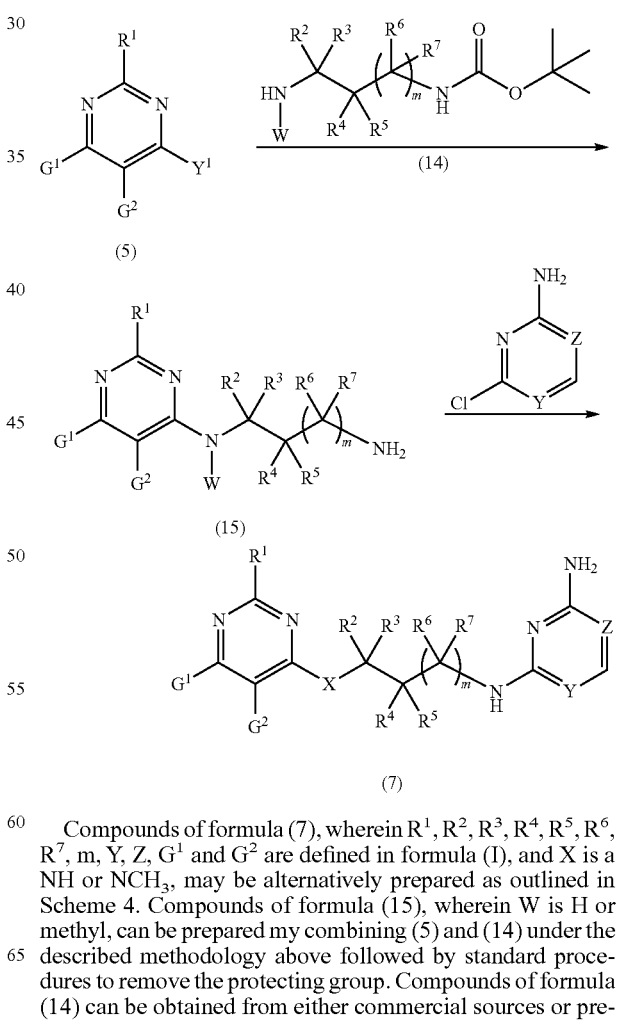

Compounds of formula (7), wherein $R^1$, $R^2$, $R^3$, $R^4$, $R^5$, $R^6$, $R^7$, m, Y, Z, $G^1$ and $G^2$ are defined in formula (I), and X is a NH or $NCH_3$, may be alternatively prepared as outlined in Scheme 4. Compounds of formula (15), wherein W is H or methyl, can be prepared my combining (5) and (14) under the described methodology above followed by standard procedures to remove the protecting group. Compounds of formula (14) can be obtained from either commercial sources or prepared by methods known to one skilled in the art of organic synthesis. Compounds of formula (7) are then prepared by the addition of chlorides such as, but not limited to, 2-amino-6-chloropyrimidine or 6-amino-2-chloropyrimidine according to the above described methodologies to afford compounds of formula (7).

Scheme 5

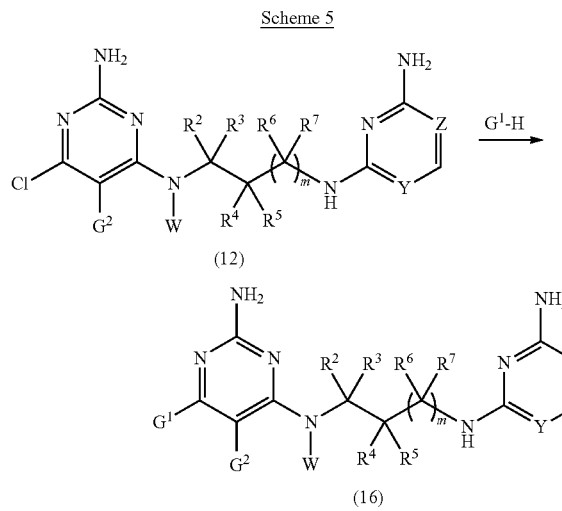

Compounds of formula (16), wherein $R^2$, $R^3$, $R^4$, $R^5$, $R^6$, $R^7$, m, Y, Z, and $G^2$ are defined in formula (I), W is H or methyl, and $G^1$ is an amine moiety, may be prepared as outlined in Scheme 5. Compounds of formula (12) may be combined with $G^1$-H, where $G^1$-H is a primary amine, under the above described methodologies in Scheme 2 to afford (16).

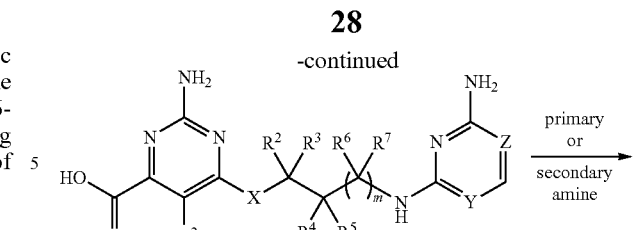

Compounds of formula (7), wherein $R^2$, $R^3$, $R^4$, $R^5$, $R^6$, $R^7$, m, Y, Z, $G^1$ and $G^2$ are defined in formula (I), and X is a nitrogen substituted with either hydrogen or methyl, and $G^1$ is an amide, may be prepared as outlined in Scheme 6. Compounds of formula (17), obtained from either commercial sources or prepared by methods known to one skilled in the art, can be combined with compounds of formula (6) according to the methodologies described in Scheme 1 to provide compounds of formula (18). The ester of compounds of formula (18) can then be hydrolyzed with lithium hydroxide by standard methodologies to provide compounds of formula (19), which are then treated with ammonia in methanol at 100° C. to afford compounds of formula (20). Compounds of formula (7), wherein $G^1$ is an amide moiety, are generated by combining a primary or secondary amine with compounds of formula (20) under standard amide coupling procedures.

Scheme 6

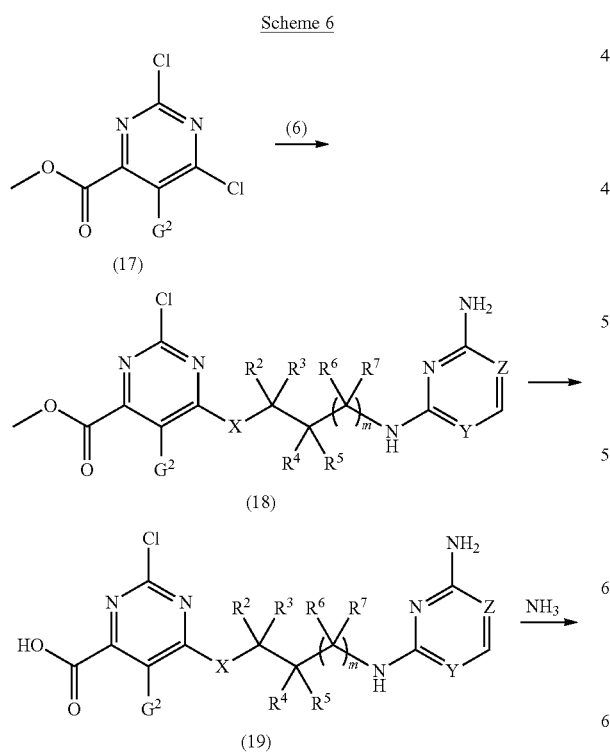

Scheme 7

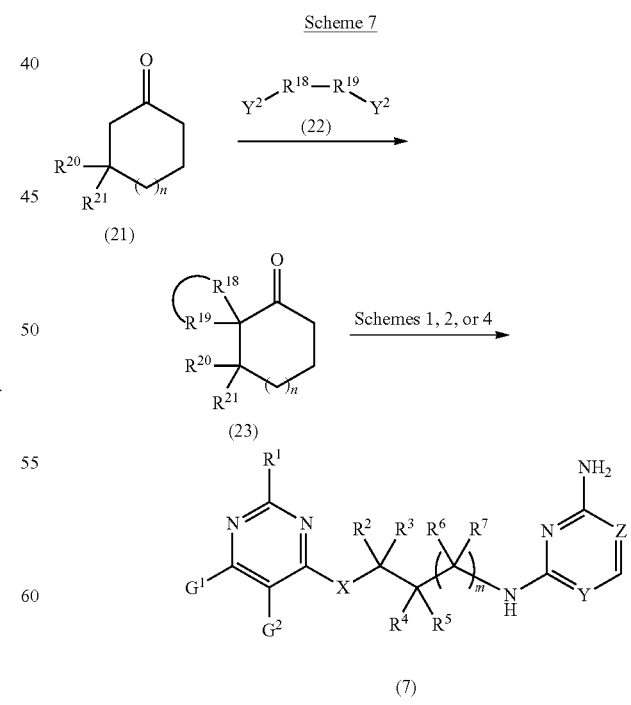

Compounds of formula (7), wherein $R_1$, $R^2$, $R^3$, $R^4$, $R^5$, $R^6$, $R^7$, m, X, Y, and Z are defined in formula (I), and wherein $G^1$ and $G^2$ are taken together as defined in formula (I) to form a group of formula (iii), and wherein $R^{18}$ and $R^{19}$ are taken together as defined in formula (I) can be prepared as outlined in Scheme 7. Compounds of formula (21) can be reacted, with or without heat, in the presence of a base such as, but not limited to, potassium tert-butoxide or sodium hydride in a solvent such as tetrahydrofuran with compounds of formula (22), wherein $Y^2$ is chloro, bromo, or iodo, to afford compounds of formula (23). Such reactions are known to those of ordinary skill in the art. Compounds of formula (23), when reacted as outlined in Schemes 1, 2, or 4, will provide compounds of formula (7), which are representative of compounds of the present invention.

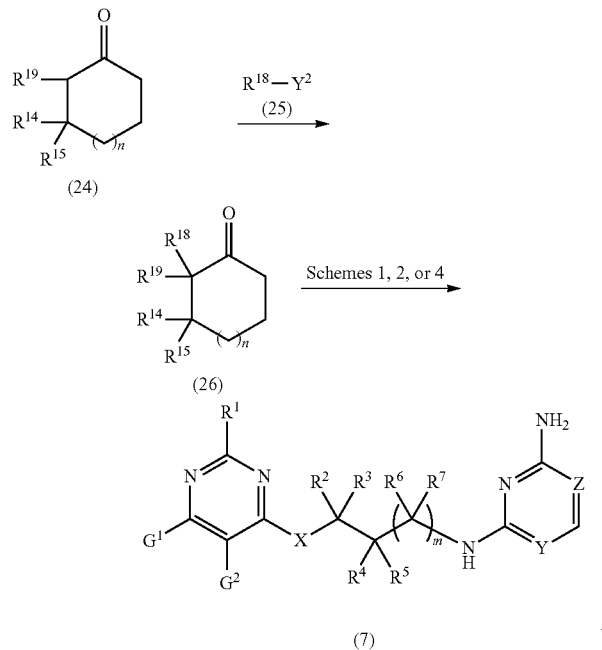

Compounds of formula (7), wherein $R_1$, $R_2$, $R_3$, $R^4$, $R_5$, $R^6$, $R_7$, m, X, Y, and Z are defined in formula (I), and wherein $G^1$ and $G^2$ are taken together as defined in formula (I) to form a group of formula (iii), and wherein $R^{19}$ is defined as in formula (I) can be prepared as outlined in Scheme 8. Compounds of formula (24) can be reacted, with or without heat, in the presence of a base such as, but not limited to, potassium tert-butoxide or sodium hydride in a solvent such as tetrahydrofuran with compounds of formula (25), wherein $R^{18}$ is alkyl and $Y^2$ is chloro, bromo, or iodo, to afford compounds of formula (26). Such reactions are known to those of ordinary skill in the art. Additionally, compounds of formula (24) can be reacted, with heat, in the presence of a base such as, but not limited to, potassium tert-butoxide or sodium hydride, in the presence of a palladium catalyst such as, but not limited to, tris(dibenzylideneacetone)dipalladium(0) chloroform adduct, in the presence of a phosphine ligand such as, but not limited to, dicyclohexyl(2',4',6'-triisopropylbiphenyl-2-yl)phosphine, in a solvent such as toluene with compounds of formula (25), wherein $R^{18}$ is aryl or heteroaryl and $Y^2$ is chloro, bromo, or iodo, to afford compounds of formula (26). Compounds of formula (26), when reacted as outlined in Schemes 1, 2, or 4, will provide compounds of formula (7), which are representative of compounds of the present invention.

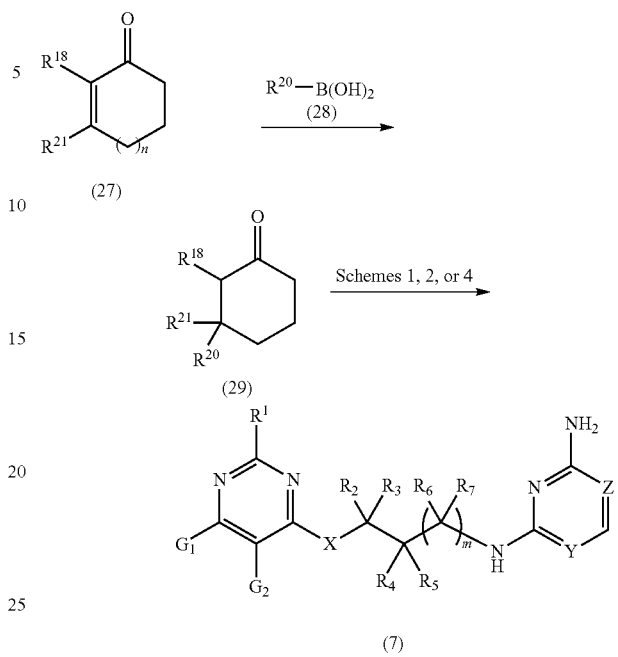

Compounds of formula (7), wherein $R^1$, $R^2$, $R^3$, $R^4$, $R^5$, $R^6$, $R^7$, m, X, Y, and Z are defined in formula (I), and wherein $G^1$ and $G^2$ are taken together as defined in formula (I) to form a group of formula (iii), and wherein $R^{18}$ and $R^{21}$ are defined as in formula (I), can be prepared as outlined in Scheme 9. Compounds of formula (27) can be reacted, with or without heat, in the presence of a base such as, but not limited to, potassium tert-butoxide or cesium carbonate, in the presence of a palladium catalyst such as, but not limited to, palladium acetate, in the presence of a phosphine ligand such as, but not limited to, triphenylphosphine, in a solvent such as toluene with compounds of formula (28), wherein $R^{20}$ is defined as aryl or heteroaryl, to afford compounds of formula (29). Such reactions are known to those of ordinary skill in the art and can be found in Chem. Lett. 2006, 35(2), 198. Compounds of formula (29), when reacted as outlined in Schemes 1, 2, or 4, will provide compounds of formula (7), which are representative of compounds of the present invention.

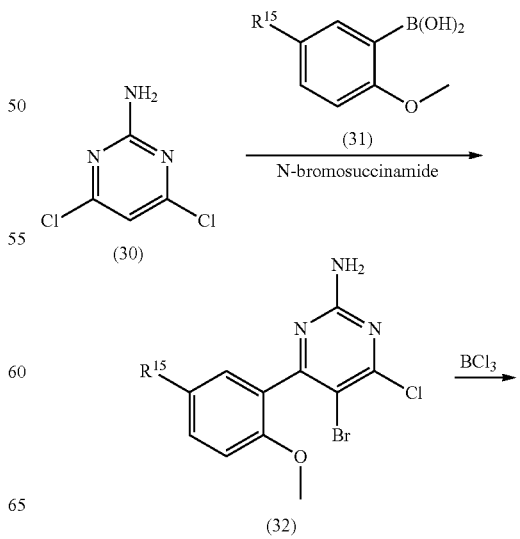

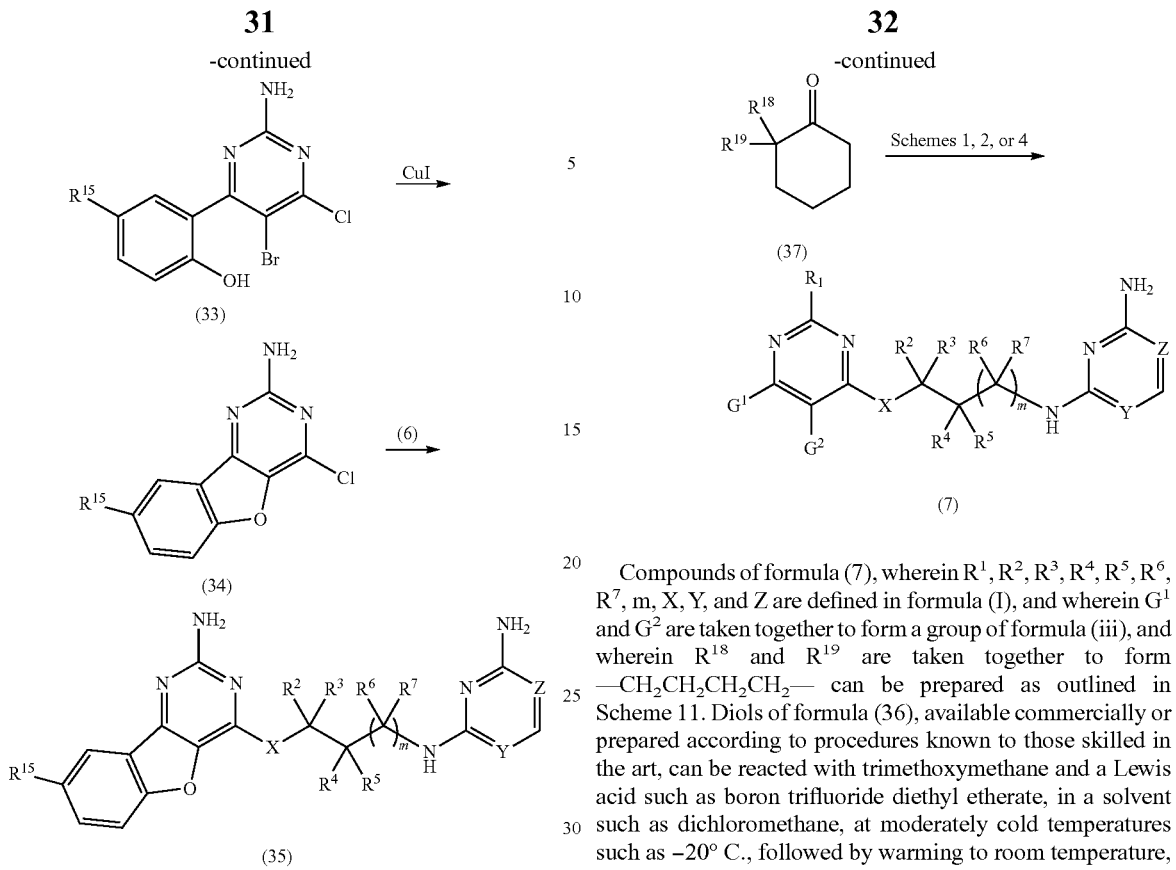

Compounds of formula (35), wherein $R^2$, $R^3$, $R^4$, $R^5$, $R^6$, $R^7$, m, X, Y, and Z are defined in formula (I), and wherein $G^1$ and $G^2$ are taken together as defined in formula (I) to form a group of formula (iv), can be prepared as outlined in Scheme 10. Compounds of formula (30) can be reacted with compounds of formula (31) under standard methodologies, followed by reaction with a brominating reagents such as, but not limited to, N-bromosuccinimide to afford compounds of formula (32). The methyl group in compounds of formula (32) can be removed by reacting with a demethylating reagent such as, but not limited to, boron trichloride to afford compounds of formula (33). Compounds of formula (34) can be formed by reacting compounds of formula (33) with a catalyst such as, but not limited to, copper(I) iodide, in the presence of a base such as, but not limited to, cesium carbonate, and in the presence of a ligand such as, but not limited to, 2,2,6,6-tetramethylheptane-3,5-dione in a solvent such as toluene. Preparation of compounds of formula (34) are described in the International Publication No. WO2007090854. Compounds of formula (34) can be reacted with compounds of formula (6) under the conditions previously described to afford compounds of formula (35).

Scheme 11

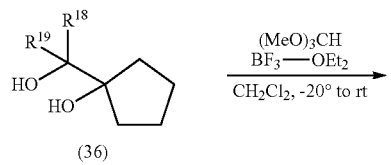

Compounds of formula (7), wherein $R^1$, $R^2$, $R^3$, $R^4$, $R^5$, $R^6$, $R^7$, m, X, Y, and Z are defined in formula (I), and wherein $G^1$ and $G^2$ are taken together to form a group of formula (iii), and wherein $R^{18}$ and $R^{19}$ are taken together to form —$CH_2CH_2CH_2CH_2$— can be prepared as outlined in Scheme 11. Diols of formula (36), available commercially or prepared according to procedures known to those skilled in the art, can be reacted with trimethoxymethane and a Lewis acid such as boron trifluoride diethyl etherate, in a solvent such as dichloromethane, at moderately cold temperatures such as −20° C., followed by warming to room temperature, to afford compounds of formula (37). Such pinacol rearrangements are well-known to those of ordinary skill in the art. Processing of compounds of formula (37) according to the procedures outlined in Schemes 1, 2, or 4 will afford compounds of (7), which are representative of compounds of the present invention.

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral, intravenous, subcutaneous, intramuscular, intraperitoneal, intra-arterial, or intradermal injection, for or for vaginal, nasal, topical, or rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals by oral administration, by injection, including by intravenous, subcutaneous, intramuscular, intraperitoneal, intra-arterial, and intradermal injection. The pharmaceutical compositions of this invention can be administered to humans and other mammals topically (as by powders, lotions, ointments or drops applied to the skin), bucally, or inhaled, as an oral or nasal spray. The pharmaceutical compositions of this invention can be administered to humans and other mammals intrarectally or intravaginally. The term "parenterally," as used herein, refers to modes of administration which include intravenous, intramuscular, intraperitoneal, intrasternal, subcutaneous and intraarticular.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents that delay absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, propionic, hydrobromic, glucuronic, methanesulfonic, ethanesulfonic, naphthalene sulfonic, lactic, fumaric, oxalic, and succinic acid.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl acid chloride. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Prodrugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

The compounds and processes of the invention will be better understood by reference to the following examples, which are intended as an illustration of and not a limitation upon the scope of the invention.

Unless otherwise described, reactions were carried out under ambient conditions (ranging 17-27° C.), under nitrogen. Unless otherwise described, column chromatography means flash chromatography carried out using silica gel, a technique well known to those of ordinary skill in the art of organic synthesis.

EXAMPLES

Example 1

$N^4$-{2-[(2-aminopyrimidin-4-yl)amino]ethyl}-6,7-dihydro-5H-benzo[6,7]cyclohepta[1,2-d]pyrimidine-2,4-diamine Example 1A methyl 5-oxo-6,7,8,9-tetrahydro-5H-benzo[7]annulene-6-carboxylate A mixture of benzosuberone (8 g, 50 mmol) and neat dimethyl carbonate (45 mL) at ambient temperature under nitrogen was treated with sodium hydride (60% in mineral oil, 4 g, 100 mmol) in 0.1 mL of dry methanol, heated at 80° C. for 3 hours, cooled to ambient temperature, treated with 2 N hydrochloric acid (55 mL) and extracted with ethyl acetate. The organic layer was washed with brine, dried (magnesium sulfate) and concentrated to provide the title compound as an oil, as a 3:1 mixture of enol and keto forms of product determined by NMR spectroscopy. The NMR of the main enol form was: $^1$H NMR (CDCl$_3$) δ 2.03-2.16 (m, 4H), 2.64 (m, 2H), 3.82 (s, 3H), 7.23 (m, 1H), 7.33 (m, 2H), 7.62 (m, 1H), 12.6 (br s, 1H); MS (ESI+) m/z 219 (M+H)$^-$.

Example 1B 2-amino-6,7-dihydro-5H-benzo[6,7]cyclohepta[1,2-d]pyrimidin-4-ol

The product from Example 1A (5.45 g, 25 mmol) was dissolved in N,N-dimethylformamide (25 mL), treated with guanidine nitrate (6.1 g, 50 mmol) and potassium carbonate (6.9 g, 50 mmol), stirred at 110° C. for 16 hours, cooled, diluted with water and neutralized to pH 6 with acetic acid. The solid was collected by filtration, washed with water and dried under vacuum to provide the title compound. $^1$H NMR (DMSO-d$_6$) δ 2.0 (m, 2H), 2.13 (t, J=6.78 Hz, 2H), 2.47 (m, 2H), 6.37 (bs, 2H), 7.25 (m, 1H), 7.31 (m, 2H), 7.53 (m, 1H), 10.83 (s, 1H); MS (ESI+) m/z 228 (M+H)$^+$.

Example 1C 4-chloro-6,7-dihydro-5H-benzo[6,7]cyclohepta[1,2-d]pyrimidin-2-amine

Example 1B (1.05 g, 4.62 mmol), triethylamine (1.1 mL, 7.85 mmol), and 4-(dimethylamino)pyridine (56 mg, 0.462 mmol) were combined in chloroform (30 mL) to form a suspension. 4-Nitrobenzene-1-sulfonyl chloride (1.54 g, 6.93 mmol) was added and the mixture was stirred overnight at room temperature. A 4 M solution of hydrochloric acid in dioxane (5.8 mL, 23.1 mmol) was added and the mixture was stirred for two hours. The mixture was diluted with ethyl acetate, washed with 1 N sodium hydroxide, washed with a saturated solution of sodium chloride, dried, and the organic layer was absorbed on silica gel and purified using silica gel chromatography (40 g column) eluting with a gradient of ethyl acetate in hexane (15-55%) to afford the title compound. $^1$H NMR (CDCl$_3$) δ 7.63-7.68 (m, 1H), 7.36-7.42 (m, 2H), 7.22-7.25 (m, 1H), 5.07 (s, 2H), 2.52-2.62 (m, 4H), 2.12-2.24 (m, 2H); MS (ESI+) m/z 246 (M+H)$^+$.

Example 1D tert-butyl 2-[(2-aminopyrimidin-4-yl)amino]ethylcarbamate tert-Butyl 2-aminoethylcarbamate (3.27 g, 20.4 mmol) and 2-amino-6-chloropyrimidine (2.38 g, 18.4 mmol) were combined in 2-methoxyethanol with triethylamine (4.3 mL, 30.3 mmol) and heated to 130° C. overnight. The mixture was diluted with methylene chloride and washed with 1 N sodium hydroxide. The aqueous layer was extracted with methylene chloride followed by ethyl acetate. The organic layers were combined, absorbed on silica gel, and purified using silica gel chromatography, eluting with a gradient of methanol in methylene chloride (1-12%) to afford the title compound. $^1$H NMR (300 MHz, CDCl$_3$) δ ppm 1.44 (s, 9H) 3.32 (q, J=5.31 Hz, 2H) 3.38-3.50 (m, 2H) 4.70 (s, 2H) 4.91-5.19 (m, 2H) 5.78 (d, J=5.76 Hz, 1H) 7.81 (d, J=5.76 Hz, 1H); MS (ESI+) m/z 253.9 (M+H)$^+$.

Example 1E

N$^4$-(2-aminoethyl)pyrimidine-2,4-diamine dihydrochloride

Example 1D (3.38 g, 13.3 mmol) was dissolved in methylene chloride (20 mL) and 4 N hydrochloric acid in dioxane (20 mL) and stirred at room temperature for one hour. The solvents were removed under reduced pressure and the resulting material was dried in a vacuum oven at 45° C. for 3 hours to afford the title compound. MS (ESI+) m/z 154.2 (M+H)$^+$.

Example 1F

N$^4$-{2-[(2-aminopyrimidin-4-yl)amino]ethyl}-6,7-dihydro-5H-benzo[6,7]cyclohepta[1,2-d]pyrimidine-2,4-diamine The product of Example 1E (155 mg, 0.686 mmol) and the product of Example 1C (140 mg, 0.571 mmol) were combined in 2-methoxyethanol (0.8 mL) and heated to 130° C. for three hours. The mixture was diluted with 1 N aqueous sodium hydroxide and extracted twice with methylene chloride. The organic layers were combined and dried over sodium sulfate and the mixture was absorbed on silica gel and purified using silica gel chromatography, eluting with a gradient of 7 N ammonia in methanol in methylene chloride (5-15%) to afford the title compound. $^1$H NMR (300 MHz, DMSO-d$_6$) δ ppm 7.62 (d, J=4.41 Hz, 1H) 7.50-7.56 (m, 1H) 7.26-7.34 (m, 2H) 7.19-7.26 (m, 1H) 6.67-6.75 (m, 1H) 5.85 (s, 2H) 5.70-5.81 (m, 4H) 3.37-3.52 (m, 4H) 2.44 (t, J=6.78 Hz, 2H) 2.08-2.18 (m, J=6.78, 6.78 Hz, 2H) 1.92-2.04 (m, 2H); MS (ESI+) m/z 363.9 (M+H)$^+$.

Example 2

N$^4$-{2-[(2-aminopyrimidin-4-yl)amino]ethyl}-N$^4$-methyl-6,7-dihydro-5H-benzo[6,7]cyclohepta[1,2-d]pyrimidine-2,4-diamine Example 2A N$^4$-[2-(methylamino)ethyl]pyrimidine-2,4-diamine dihydrochloride tert-Butyl 2-aminoethyl(methyl)carbamate (337 mg, 1.93 mmol) and 4-chloropyrimidin-2-amine (260 mg, 2.01 mmol) were combined under the conditions described in Example 1D to afford tert-butyl 2-[(2-aminopyrimidin-4-yl)amino]ethyl(methyl)carbamate. MS (M+H)$^+$ m/z 268.3. The intermediate was treated under the conditions of Example 1E to afford the title compound. MS (ESI+) m/z 167.9 (M+H)$^+$.

Example 2B

N$^4$-{2-[(2-aminopyrimidin-4-yl)amino]ethyl}-N$^4$-methyl-6,7-dihydro-5H-benzo[6,7]cyclohepta[1,2-d]pyrimidine-2,4-diamine The product from Example 2A (95 mg, 0.237 mmol) and the product of Example 1C (50 mg, 0.203 mmol) were combined under the conditions described in Example 1F to afford the title compound. $^1$H NMR (300 MHz, DMSO-d$_6$) δ ppm 7.62-7.67 (m, 1H) 7.58 (d, J=5.43 Hz, 1H) 7.28-7.37 (m, 2H) 7.23-7.28 (m, 1H) 6.89 (s, 1H) 5.94 (s, 2H) 5.82 (s, 2H) 5.70 (d, J=5.76 Hz, 1H) 3.43-3.55 (m, 4H) 2.99-3.04 (m, 3H) 2.50-2.58 (m, 2H) 2.15 (dd, J=16.11, 5.93 Hz, 4H); MS (ESI+) m/z 377.0 (M+H)$^+$.

Example 3

N$^4$-{3-[(2-aminopyrimidin-4-yl)amino]propyl}-6,7-dihydro-5H-benzo[6,7]cyclohepta[1,2-d]pyrimidine-2,4-diamine Example 3A tert-butyl 3-[(2-amino-6,7-dihydro-5H-benzo[6,7]cyclohepta[1,2-d]pyrimidin-4-yl)amino]propylcarbamate tert-Butyl 3-aminopropylcarbamate (120 mg, 0.690 mmol) and the product from Example 1C (113 mg, 0.460 mmol) were treated under the conditions described in Example 1D to afford the title compound. $^1$H NMR (300 MHz, CDCl$_3$) δ ppm 1.47 (s, 9H) 1.65-1.81 (m, 2H) 2.06-2.27 (m, 4H) 2.58 (t, J=6.74 Hz, 2H) 3.22 (q, J=5.95 Hz, 2H) 3.56 (q, J=6.08 Hz, 2H) 4.93 (s, 2H) 5.47-5.76 (m, 2H) 7.16-7.23 (m, 1H) 7.28-7.40 (m, 2H) 7.64-7.71 (m, 1H); MS (ESI+) m/z 384.1 (M+H)$^+$.

Example 3B

N$^4$-(3-aminopropyl)-6,7-dihydro-5H-benzo[6,7]cyclohepta[1,2-d]pyrimidine-2,4-diamine The product from Example 3A was treated under the conditions of Example 1E to afford the title compound. $^1$H NMR (300 MHz, DMSO-d$_6$) δ ppm 1.84-1.99 (m, 2H) 2.07-2.21 (m, 2H) 2.28 (t, J=6.61 Hz, 2H) 2.60 (t, J=6.78 Hz, 2H) 2.78-2.92 (m, 2H) 3.52 (q, J=6.10 Hz, 2H) 7.39-7.56 (m, 3H) 7.57-7.63 (m, 1H) 7.62-7.80 (m, 1H) 7.95-8.19 (m, 3H) 8.71 (s, 1H); MS (ESI+) m/z 283.9 (M+H)$^+$.

Example 3C

N$^4$-{3-[(2-aminopyrimidin-4-yl)amino]propyl}-6,7-dihydro-5H-benzo[6,7]cyclohepta[1,2-d]pyrimidine-2,4-diamine The product of Example 3B (45 mg, 0.126 mmol) and 2-amino-6-chloropyrimidine (21 mg, 0.164 mmol) were treated under the conditions described in Example 1F to afford the title compound. $^1$H NMR (300 MHz, CDCl$_3$) δ ppm 7.86 (d, J=5.16 Hz, 1H) 7.64-7.70 (m, 1H) 7.28-7.40 (m, 2H) 7.17-7.23 (m, 1H) 5.77 (d, J=5.95 Hz, 1H) 5.30 (s, 1H) 5.02 (t, J=5.55 Hz, 1H) 4.63 (s, 2H) 3.59 (q, J=6.35 Hz, 2H) 3.32 (d, J=5.16 Hz, 2H) 2.58 (t, J=6.54 Hz, 2H) 2.05-2.24 (m, 4H) 1.83-1.96 (m, 2H); MS (ESI+) m/z 377.0 (M+H)$^+$.

Example 4

N$^4$-{2-[(4-aminopyrimidin-2-yl)amino]ethyl}-6,7-dihydro-5H-benzo[6,7]cyclohepta[1,2-d]pyrimidine-2,4-diamine Example 4A tert-butyl 2-[(2-amino-6,7-dihydro-5H-benzo[6,7]cyclohepta[1,2-d]pyrimidin-4-yl)amino]ethylcarbamate tert-Butyl 2-aminoethylcarbamate (595 mg, 3.71 mmol) and the product from Example 1C (702 mg, 2.86 mmol) were treated under the conditions described in Example 1D to afford the title compound. $^1$H NMR (300 MHz, DMSO-$d_6$) δ ppm 1.38 (s, 9H) 1.97-2.08 (m, 2H) 2.15 (t, J=6.27 Hz, 2H) 2.43-2.49 (m, 2H) 3.15 (q, J=6.22 Hz, 2H) 3.33-3.42 (m, 2H) 5.84 (s, 2H) 6.68 (s, 1H) 6.89 (t, J=5.43 Hz, 1H) 7.20-7.27 (m, 1H) 7.27-7.37 (m, 2H) 7.49-7.57 (m, 1H); MS (ESI+) m/z 370.0 (M+H)$^+$.

Example 4B

N$^4$-(2-aminoethyl)-6,7-dihydro-5H-benzo[6,7]cyclohepta[1,2-d]pyrimidine-2,4-diamine dihydrochloride The product of Example 4A (421 mg, 1.14 mmol) was treated under the conditions of Example 1E to afford the title compound. $^1$H NMR (300 MHz, DMSO-$d_6$) δ ppm 2.18 (d, J=6.44 Hz, 2H) 2.28 (d, J=6.10 Hz, 2H) 2.61 (t, J=6.44 Hz, 2H) 3.06-3.16 (m, 2H) 3.64-3.74 (m, 2H) 7.39-7.54 (m, 3H) 7.56-7.63 (m, 1H) 7.63-7.82 (m, 1H) 8.15 (s, 3H) 8.66 (t, J=5.09 Hz, 1H); MS (ESI+) m/z 269.9 (M+H)$^-$.

Example 4C

N$^4$-{2-[(4-aminopyrimidin-2-yl)amino]ethyl}-6,7-dihydro-5H-benzo[6,7]cyclohepta[1,2-d]pyrimidine-2,4-diamine The product of Example 4B (67 mg, 0.196 mmol) and 6-amino-2-chloropyrimidine (33 mg, 0.254 mmol) were treated under the conditions of Example 1F to afford the title compound. $^1$H NMR (300 MHz, CDCl$_3$) δ ppm 7.87 (d, J=5.55 Hz, 1H) 7.62-7.68 (m, 1H) 7.28-7.37 (m, 2H) 7.14-7.21 (m, 1H) 5.80 (d, J=5.55 Hz, 1H) 5.30-5.39 (m, 1H) 4.72 (s, 2H) 4.61 (s, 2H) 3.57-3.73 (m, 4H) 2.53 (t, J=6.94 Hz, 2H) 2.15 (t, J=6.35 Hz, 2H) 1.94-2.08 (m, 2H); MS (ESI+) m/z 363.0 (M+H)$^+$.

Example 5

N$^4$-{2-[(2-aminopyrimidin-4-yl)amino]ethyl}-6-phenylpyrimidine-2,4-diamine

The product of Example 1E (73 mg, 0.323 mmol) and 4-chloro-6-phenylpyrimidin-2-amine (51 mg, 0.248 mmol) were treated under the conditions of Example 1F to afford the title compound. $^1$H NMR (300 MHz, DMSO-$d_6$) δ ppm 7.84-7.93 (m, J=7.12, 2.37 Hz, 2H) 7.57-7.66 (m, 1H) 7.39-7.48 (m, 3H) 6.81-7.14 (m, 2H) 6.24 (s, 1H) 6.04 (s, 2H) 5.90 (s, 2H) 5.74 (d, J=5.76 Hz, 1H) 3.35-3.48 (m, 4H); MS (ESI+) m/z 323.0 (M+H)$^+$.

Example 6

N$^4$-{2-[(2-aminopyrimidin-4-yl)amino]ethyl}-6-(3-chlorophenyl)pyrimidine-2,4-diamine

Example 6A

N$^4$-{2-[(2-aminopyrimidin-4-yl)amino]ethyl}-6-chloropyrimidine-2,4-diamine

The product of Example 1E (250 mg, 1.11 mmol) and 2-amino-4,6-dichloropyrimidine (201 mg, 1.23 mmol) were treated under the conditions described in Example 1F to afford the title compound. $^1$H NMR (300 MHz, DMSO-$d_6$) δ ppm 3.31-3.41 (m, 4H) 5.72 (d, J=5.95 Hz, 1H) 5.75 (s, 1H) 5.85 (s, 2H) 6.40 (s, 2H) 6.85 (s, 1H) 7.21 (s, 1H) 7.61 (d, J=5.55 Hz, 1H); MS (ESI+) m/z 280.9 (M+H)$^+$.

Example 6B

N$^4$-{2-[(2-aminopyrimidin-4-yl)amino]ethyl}-6-(3-chlorophenyl)pyrimidine-2,4-diamine The product of Example 6A (69 mg, 0.246 mmol), 3-chlorophenylboronic acid (42 mg, 0.270 mmol), dichlorobis((triphenylphosphine)palladium(II) (17 mg, 0.025 mmol), and potassium carbonate (100 mg, 0.724 mmol) were combined with dioxane (5 mL) and water (1.5 mL) and heated to 100° C. overnight. The mixture was diluted with methylene chloride, washed with water, and absorbed on silica gel and purified using silica gel chromatography, eluting with a gradient of 7 N ammonia in methanol in methylene chloride (5-15%) to afford the title compound. $^1$H NMR (300 MHz, DMSO-$d_6$) δ ppm 7.98 (s, 1H) 7.76-7.86 (m, 1H) 7.61 (d, J=5.76 Hz, 1H) 7.41-7.52 (m, 2H) 7.00 (s, 1H) 6.86 (s, 1H) 6.28 (s, 1H) 6.08 (s, 2H) 5.85 (s, 2H) 5.69-5.77 (m, 1H) 3.33-3.50 (m, 4H); MS (ESI+) m/z 356.9 (M+H)$^+$.

Example 7

N$^4$-{2-[(2-aminopyrimidin-4-yl)amino]ethyl}-6-(3,5-dichlorophenyl)pyrimidine-2,4-diamine The product of Example 6A (62 mg, 0.221 mmol) and 3,5-dichlorophenyl boronic acid (46 mg, 0.243 mmol) were treated under the conditions described in Example 6B to afford the title compound. $^1$H NMR (300 MHz, DMSO-$d_6$) δ ppm 7.92 (s, 2H) 7.66 (t, J=2.03 Hz, 1H) 7.61 (d, J=5.76 Hz, 1H) 6.99 (s, 1H) 6.86 (s, 1H) 6.33 (s, 1H) 6.15 (s, 2H) 5.85 (s, 2H) 5.74 (d, J=5.76 Hz, 1H) 3.33-3.51 (m, 4H); MS (ESI+) m/z 390.9 (M+H)$^+$.

Example 8

N$^4$-{2-[(2-aminopyrimidin-4-yl)amino]ethyl}-6-(5-chloro-2-methoxyphenyl)pyrimidine-2,4-diamine The product of Example 6A (50 mg, 0.178 mmol) and 5-chloro-2-methoxyphenyl boronic acid (37 mg, 0.196 mmol) were treated under the conditions described in Example 6B to afford the title compound. $^1$H NMR (300 MHz, DMSO-$d_6$) δ ppm 7.85 (d, J=2.78 Hz, 1H) 7.61 (d, J=5.55 Hz, 1H) 7.39 (dd, J=8.92, 2.97 Hz, 1H) 7.12 (d, J=8.73 Hz, 1H) 7.02 (s, 1H) 6.88 (s, 1H) 6.42 (s, 1H) 5.97 (s, 2H) 5.86 (s, 2H) 5.74 (d, 1H) 3.82 (s, 3H) 3.34-3.43 (m, 4H); MS (ESI+) m/z 387.2 (M+H)$^+$.

Example 9

N$^4$-{2-[(2-aminopyrimidin-4-yl)amino]ethyl}-6-[(E)-2-phenylvinyl]pyrimidine-2,4-diamine The product of Example 6A (57 mg, 0.203 mmol) and (E)-styrylboronic acid (33 mg, 0.223 mmol) were treated under the conditions described in Example 6B to afford the title compound. $^1$H NMR (300 MHz, DMSO-$d_6$) δ ppm 7.48-7.65 (m, 4H) 7.26-7.43 (m, 3H) 6.76-7.02 (m, J=15.86 Hz, 3H) 5.80-5.94 (m, 5H) 5.74 (d, J=5.95 Hz, 1H) 3.34-3.43 (m, 4H); MS (ESI+) m/z 349.0 (M+H)+.

Example 10

N4'-{2-[(2-aminopyrimidin-4-yl)amino]ethyl}-6',7'-dihydro-5'H-spiro[cyclopentane-1,8'-quinazoline]-2',4'-diamine Example 10A spiro[4.5]decan-6-one To a solution of bi(cyclopentane)-1,1'-diol (5.16 g, 29.4 mmol) in methylene chloride (80 mL), cooled to −20° C., was added trimethoxymethane (3.22 mL, 29.4 mmol), followed by boron trifluoride etherate (2.98 mL, 23.52 mmol). The cold bath was removed, and the reaction was stirred at ambient temperature for 2 hours. The mixture was then diluted with methylene chloride (100 mL), washed with saturated sodium bicarbonate, dried with magnesium sulfate, and concentrated under reduced pressure. The resulting residue was chromatographed on silica gel (100% hexane to 15:85 ethyl acetate/hexane, eluant) to provide the title compound. $^1$H NMR (300 MHz, CDCl$_3$) δ 2.40 (t, 2H), 2.00-2.11 (m, 2H), 1.78-1.87 (m, 2H), 1.71 (t, 4H), 1.59 (t, 4H), 1.39 (t, 2H); MS (DCI+) m/z 153 (M+H)+.

Example 10B methyl 6-oxospiro[4.5]decane-7-carboxylate

A solution of diisopropylamine (5.97 mL, 41.9 mmol) in ether (30 mL) was cooled to −78° C. and then was treated slowly with n-butyllithium (16.75 mL, 41.9 mmol). The mixture was stirred at −78° C. for 30 minutes; then this solution was transferred via cannula into a −78° C. solution of Example 10A (4.25 g, 27.9 mmol) in ether (30 mL). The mixture was stirred at this temperature for 30 minutes and then was treated with dimethyl carbonate (23.50 mL, 279 mmol). The resulting mixture was warmed to ambient temperature and stirred for 16 hours. The mixture was quenched with saturated ammonium chloride and diluted with ether (100 mL); then the layers were separated. The aqueous layer was extracted with additional ether, then the organic layers were combined, dried with magnesium sulfate, and concentrated under reduced pressure. The residue was chromatographed on silica gel (100% hexane to 85:15 ethyl acetate/hexanes, eluant) to provide the title product. $^1$H NMR (300 MHz, CDCl$_3$) δ 12.40-12.42 (m, 1H), 3.72-3.76 (m, 3H), 2.18-2.26 (m, 2H), 2.00-2.12 (m, 2H), 1.74-1.86 (m, 2H), 1.57-1.62 (m, 2H), 1.54-1.57 (m, 2H), 1.35-1.48 (m, 4H); MS (DCI+) m/z 211 (M+H)+.

Example 10C

2'-amino-6',7'-dihydro-5'H-spiro[cyclopentane-1,8'-quinazolin]-4'-ol

A solution of Example 10B (4.5 g, 21.4 mmol), guanidine hydrochloride (6.13 g, 64.2 mmol), and potassium carbonate (9.46 g, 68.5 mmol) in N,N-dimethylformamide (30 mL) was heated at 105-110° C. for 3 hours. The mixture was then filtered through a layer of diatomaceous earth, and the filter pad was washed with a small amount of N,N-dimethylformamide. Approximately two volumes of water were then added, and the pH of the resulting mixture was adjusted to pH 6-7 with acetic acid. The precipitate was collected, washed with water, and dried under vacuum to provide the title product. $^1$H NMR (300 MHz, DMSO-d$_6$) δ 10.50-10.61 (m, 1H), 5.98-6.08 (m, 2H), 2.20 (t, 2H), 1.95-2.04 (m, 2H), 1.68-1.76 (m, 2H), 1.61-1.68 (m, 2H), 1.48-1.58 (m, 4H), 1.34-1.45 (m, 2H); MS (DCI+) m/z 220 (M+H)+.

Example 10D

2'-amino-6',7'-dihydro-5'H-spiro[cyclopentane-1,8'-quinazolin]-4'-yl 4-methylbenzenesulfonate A solution of Example 10C (2.91 g, 13.27 mmol), p-toluenesulfonyl chloride (3.79 g, 19.91 mmol), and 4-(dimethylamino)pyridine (324 mg, 2.65 mmol) in methylene chloride (60 mL) was treated with triethylamine (3.7 mL, 4.40 mmol) at ambient temperature, and the resulting solution was stirred for 3 hours. It was then diluted with methylene chloride (100 mL) and water (50 mL), and the layers were separated. The organic layer was dried with magnesium sulfate and concentrated under reduced pressure; then the residue was chromatographed on silica gel (1:2:2 ethyl acetate/methylene chloride/hexane, eluant) to provide the title product. $^1$H NMR (300 MHz, CD$_3$OD) δ 7.95 (d, 2H), 7.44 (d, 2H), 2.45-2.47 (m, 3H), 2.40-2.45 (m, 2H), 1.99-2.10 (m, 2H), 1.79-1.90 (m, 2H) 1.65-1.75 (m, 6H), 1.52-1.62 (m, 2H); MS (DCI+) m/z 374 (M+H)+.

Example 10E

N4'-{2-[(2-aminopyrimidin-4-yl)amino]ethyl}-6',7'-dihydro-5'H-spiro[cyclopentane-1,8'-quinazoline]-2',4'-diamine The product from Example 10D (61 mg, 0.163 mmol) and the product from Example 1E (44 mg, 0.195 mmol) were treated under the conditions of Example 1F to afford the title compound. $^1$H NMR (300 MHz, DMSO-d$_6$) δ ppm 1.41 (dd, J=11.19, 5.43 Hz, 2H) 1.47-1.57 (m, 2H) 1.57-1.69 (m, 4H) 1.69-1.83 (m, 2H) 1.96-2.09 (m, 2H) 2.16 (t, J=5.93 Hz, 2H) 3.33-3.52 (m, 4H) 5.45 (s, 2H) 5.66-5.77 (m, 1H) 5.84 (s, 2H) 6.20 (s, 1H) 6.89 (s, 1H) 7.61 (d, J=5.09 Hz, 1H); MS (ESI+) m/z 355.0 (M+H)+.

Example 11

N4-{2-[(2-aminopyrimidin-4-yl)amino]ethyl}-8-phenyl-6,7,8,9-tetrahydro-5H-cyclohepta[d]pyrimidine-2,4-diamine Example 11A methyl 2-oxo-4-phenylcycloheptanecarboxylate A mixture of 3-phenylcycloheptanone (1.88 g, 9.99 mmol) and 5 drops of methanol in dimethyl carbonate (1.68 mL, 20.0 mmol) was treated with sodium hydride (60% dispersion, 800 mg, 20.0 mmol). The reaction was then refluxed for 2 hours before being cooled back to room temperature. The reaction was quenched with 2 M hydrochloric acid and extracted with ether, then chromatographed on silica gel (15% ethyl acetate/hexane, eluant) to afford the title compound as a colorless oil. $^1$H NMR (300 MHz, DMSO-d$_6$) δ 7.26 (m, 5H), 3.81 (dd, J=11.70, 3.77 Hz, 1H), 3.63 (s, 3H), 3.17 (m, 2H), 1.86 (m, 6H); MS (DCI+) m/z 247 (M+H)+, 264 (M+NH$_4$)+.

Example 11B

2-amino-8-phenyl-6,7,8,9-tetrahydro-5H-cyclohepta[d]pyrimidin-4-ol

A mixture of Example 11A (1.86 g, 7.55 mmol), guanidine nitrate (1.84 g, 15.1 mmol), and potassium carbonate (2.09 g, 15.1 mmol) was heated in N,N-dimethylformamide (7.5 mL) at 120° C. overnight. After this time, the mixture was cooled to room temperature and poured into water. The liquid was adjusted to pH 5 with acetic acid, then the precipitate was collected by filtration, washed with water, and air-dried. It was further dried by azeotroping with toluene to yield the title compound. $^1$H NMR (300 MHz, DMSO-$d_6$) δ 10.73 (m, 1H), 7.26 (m, 5H), 6.26 (s, 2H), 3.10 (s, 1H), 3.00 (dd, J=14.67, 6.35 Hz, 1H), 2.60 (t, J=13.68 Hz, 1H), 2.39 (d, J=13.48 Hz, 1H), 2.10 (m, 1H), 1.88 (m, 3H), 1.22 (m, 1H); MS (DCI$^+$) m/z 256 (M+H)$^+$.

Example 11C

2-amino-8-phenyl-6,7,8,9-tetrahydro-5H-cyclohepta[d]pyrimidin-4-yl 4-methylbenzenesulfonate

Example 11B (1.25 g, 4.90 mmol), p-toluenesulfonyl chloride (1.87 g, 9.79 mmol), and triethylamine (2.05 mL, 14.7 mmol) were stirred in dichloromethane (50 mL) overnight at room temperature. The reaction mixture was diluted with methylene chloride after this time and then washed three times with water. The solution was dried over sodium sulfate and evaporated, then the residue was chromatographed on silica gel (15 to 100% ethyl acetate/hexane, eluant) to give the title compound. $^1$H NMR (300 MHz, DMSO-$d_6$) δ 7.99 (d, J=8.14 Hz, 2H), 7.49 (d, J=8.14 Hz, 2H), 7.24 (m, 5H), 6.68 (s, 2H), 3.37 (m, 1H), 2.80 (dd, J=15.09, 5.93 Hz, 1H), 2.63 (d, J=13.56 Hz, 2H), 2.44 (s, 3H), 2.39 (d, J=14.58 Hz, 1H), 1.92 (m, 3H), 1.23 (m, J=10.51 Hz, 1H); MS (DCI$^-$) m/z 410 (M+H)$^-$.

Example 11D

N$^4$-{2-[(2-aminopyrimidin-4-yl)amino]ethyl}-8-phenyl-6,7,8,9-tetrahydro-5H-cyclohepta[d]pyrimidine-2,4-diamine

The product from Example 11C (102 mg, 0.248 mmol) and the product from Example 1E (73 mg, 0.323 mmol) were treated under the conditions of Example 1F to afford the title compound. $^1$H NMR (300 MHz, DMSO-$d_6$) δ ppm 1.09-1.29 (m, 2H) 1.70-2.02 (m, 3H) 2.22-2.63 (m, 2H) 2.71 (dd, J=15.47, 5.16 Hz, 1H) 3.06-3.27 (m, 2H) 3.34-3.50 (m, 3H) 5.56-5.65 (m, 2H) 5.70-5.78 (m, 1H) 5.87 (s, 2H) 6.52 (s, 1H) 6.90 (s, 1H) 7.10-7.34 (m, 5H) 7.61 (d, J=5.55 Hz, 1H); MS (ESI+) m/z 391.1 (M+H)$^+$.

Example 12

N$^4$-[2-([1]benzofuro[3,2-d]pyrimidin-4-ylamino)ethyl]pyrimidine-2,4-diamine

4-Chloro-benzo[4,5]furo[3,2-d]pyrimidine (50 mg, 0.244 mmol) and the product of Example 1E (72 mg, 0.318 mmol) were treated under the conditions of Example 1F to afford the title compound. $^1$H NMR (300 MHz, DMSO-$d_6$) δ ppm 3.59-3.85 (m, 4H) 6.03 (d, J=7.12 Hz, 1H) 7.52 (t, J=7.46 Hz, 1H) 7.58-7.67 (m, 1H) 7.67-7.88 (m, 4H) 8.11 (d, J=7.12 Hz, 1H) 8.28-8.44 (m, 1H) 8.82 (t, J=5.43 Hz, 1H) 11.69 (s, 1H); MS (ESI+) m/z 322.0 (M+H)$^+$.

Determination of Biological Activity

There are many methods available to show the effectiveness of compounds as histamine H$_4$ receptor ligands. Histamine H$_4$ receptors from mammalian species have been cloned. Methods to clone, express, and assess the potency and functional activity of such cloned genes are well known to those skilled in the art of molecular biology. Examples of methods of cloning and expressing histamine H$_4$ receptors, and of assessing the potency and functional activity are described in Nguyen, et al. Molecular Pharmacology (2001) vol. 59 pp. 427-433; Zhu, et al. Molecular Pharmacology (2001) vol. 59 pp. 434-441; Coge, et al., Biochemical and Biophysical Research Communications (2001) vol. 284, pp. 301-309; Liu, et al. Molecular Pharmacology (2001) vol. 59 pp. 420-426; Liu, et al. Journal of Pharmacology and Experimental Therapeutics (2001) v. 299, pp. 121-130; and Thurmond, et al. Journal of Pharmacology and Experimental Therapeutics (2004) v. 309, pp. 404-413. In the present case, to determine the potency and effectiveness of representative compounds of this invention as histamine-H$_4$ receptor ligands (H$_4$ receptor ligands), the following tests were conducted according to previously described methods (see Esbenshade, et al., Biochemical Pharmacology (2004), vol. 68, pp. 933-945, and in Krueger, et al., Journal of Pharmacology and Experimental Therapeutics (2005) v. 314, pp. 271-281): histamine H$_4$ receptors were cloned and stably expressed in HEK-293 (human embryonic kidney) cells coexpressing a Gαqi5. Before testing, cells are loaded with a Ca$^{+2}$ sensitive fluorescent dye, in this case Fluo-4 (Invitrogen, Carlsbad, Calif.). In the case of partial agonist or agonist ligands, addition of compound to the cells leads to the increase in intracellular Ca$^{+2}$ which is detected by FLIPR (Fluorescence Imaging Plate Reader; Molecular Devices, Sunnyvale, Calif.) technology. In a similar manner, compounds that are antagonists or inverse agonists, block the increase in fluorescence induced by the full histamine H$_4$ agonist histamine, and partial agonists reduce the amount of fluorescence induced by the full histamine H$_4$ agonist histamine. The fluorescence intensities measured before addition of the test compound are subtracted from the fluorescence intensities at later time points. Peak response values determined at each concentration of ligand are expressed as a percentage of the response obtained with the full agonist histamine. Concentration versus response data are analyzed to obtain compound potency as K$_b$ values for antagonists and inverse agonists and as EC$_{50}$ values for partial agonists.

TABLE 1

| In vitro histamine H$_4$ potency of compounds in FLIPR | |
|---|---|
| Example # | Potency (nM) |
| 1 | 204 |
| 2 | 25 |
| 3 | 309 |
| 4 | 1349 |
| 5 | 8.7 |
| 6 | 2.5 |
| 7 | 69 |
| 8 | 589 |
| 9 | 85 |
| 10 | 32 |
| 11 | 2344 (EC$_{50}$) |
| 12 | 2089 |

Representative compounds of the invention demonstrated potencies in the above FLIPR assay from about 2.5 nM to 2344 nM. Preferred compounds of the invention have potencies at histamine-$H_4$ receptors from about 2.5 nM to about 200 nM.

The potency of compounds of the invention in displacing $^3$H-histamine in competition binding assays is assessed by methods described in Esbenshade, et al., Biochemical Pharmacology (2004), vol. 68, pp. 933-945. In this assay, membranes were prepared from HEK-293 cells transiently transfected with the pCINeo expression vector harboring the histamine $H_4$ receptor by homogenization of the cells on ice in TE buffer (50 mM Tris-HCl buffer, pH 7.4, containing 5 mM EDTA), 1 mM benzamidine, 2 μg/mL aprotinin, 1 μg/mL leupeptin, and 1 μg/mL pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer. Competition radioligand binding assays were performed with increasing concentrations of test compound in the presence of [$^3$H]-histamine incubated at 25° C. for 1 hour in a total volume of 0.5 mL of 50 mM Tris, 5 mM EDTA, pH 7.4. All binding reactions were terminated by filtration under vacuum onto polyethylenimine (0.3%) presoaked Unifilters (PerkinElmer Life Sciences) or Whatman GF/B filters (Whatman, Clifton, N.J.) followed by three brief washes with 4 mL of ice-cold TE buffer. Bound radiolabel was determined by liquid scintillation counting. For all of the radioligand competition binding assays, $IC_{50}$ values and Hill slopes were determined by Hill transformation of the data and $K_i$ values were determined by the Cheng-Prusoff equation. The following table of representative histamine $H_4$ receptor ligands is provided, along with potency values:

| Compound Name (Example number) | Potency (nM) |
|---|---|
| $N^4$-{2-[(2-aminopyrimidin-4-yl)amino]ethyl}-$N^4$-methyl-6,7-dihydro-5H-benzo[6,7]cyclohepta[1,2-d]pyrimidine-2,4-diamine (Example 2) | 3.5 |
| $N^4$-{2-[(2-aminopyrimidin-4-yl)amino]ethyl}-6-(3-chlorophenyl)pyrimidine-2,4-diamine (Example 6) | 6.6 |
| $N^4$-{2-[(2-aminopyrimidin-4-yl)amino]ethyl}-6-[(E)-2-phenylvinyl]pyrimidine-2,4-diamine (Example 9) | 20 |
| $N^{4'}$-{2-[(2-aminopyrimidin-4-yl)amino]ethyl}-6',7'-dihydro-5'H-spiro[cyclopentane-1,8'-quinazoline]-2',4'-diamine (Example 10) | 7.4 |

Generally, representative compounds of the invention demonstrate potencies from about 3.5 nM to about 26000 nM. Preferred compounds of the invention have potencies at histamine-$H_4$ receptors from about 3.5 nM to about 200 nM.

In addition to the utility of in vitro methods for characterizing the potency of compounds at the $H_4$ receptor, there are animal disease models of available which demonstrate the utility of compounds. There are a number of methods to test the activity of compounds in different pain models that are well known to those skilled in the art. A description of the formalin test in rats, as neuropathic pain models in rats, and general descriptions of methods of testing and descriptions of pain models are found in the book 'Drug Discovery and Evaluation, $2^{nd}$ edition' (H. Gerhard Vogel, editor; Springer-Verlag, New York, 2002; pp. 702-706).

The usefulness of histamine $H_4$ receptor ligands in treating pain has been demonstrated (Coruzzi, et al, *Eur. J. Pharmacol.* 2007, 563, 240-244). This invention discloses the utility of the compounds of the invention to treat pain, including multiple types of pain, including inflammatory pain, non-inflammatory pain, and neuropathic pain. Neuropathic pain is distinct from other types of pain (e.g. inflammatory pain), and can develop in response to previous or ongoing tissue injury, nerve injury, or diabetes, but persists long after signs of the original injury or damage have disappeared. Neuropathic pain is not well treated currently and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell Expert Opinion on Emerging Drugs (2005) vol. 10(1), pp. 95-108; Vinik and Mehrabyan Medical Clinics of North America (2004), vol. 88(4), pp. 947-999; Dray, Urban, and Dickenson Trends in Pharmacological Sciences (1994) vol. 15(6) pp. 190-7; Dworkin Clinical Journal of Pain (2002) vol. 18(6) pp. 343-9. There do exist a number of animal models of neuropathic pain that can be used to assess the ability of the compounds of the invention to treat neuropathic pain, as discussed herein.

Animal models of neuropathic pain are predictive of efficacy of treatment of neuropathic pain in humans. These models are used to assess the efficacy of compounds of the invention in treating neuropathic pain. Examples of models well known to those skilled in the art include the Chung model (Kim and Chung, Pain (1992) vol. 50 pp. 355-363) and the Bennett model (Bennett and Xie, Pain (1988) vol. 30 pp. 87-107).

Determination of Analgesic Effect Against Neuropathic Pain

Animals were prepared for testing, by use of a surgical procedure that induces neuropathic pain in one paw. Male Sprague Dawley rats were purchased from Charles River (Portage, Mich.). Prior to surgery, animals were housed in groups and maintained in a temperature-regulated environment. Following nerve ligation surgery, animals were housed in groups, and had access to food and water ad libitum.

The L5 and L6 spinal nerves of anesthetized rats were tightly ligated in a manner described previously (see Kim and Chung, Pain (1992) vol. 50 pp. 355-363). An incision was made on the dorsal portion of the hip and the muscle was blunt-dissected to reveal the spinal processes. The L6 transverse process was removed, and the left side L5 and L6 spinal nerves were tightly ligated with 5.0 braided silk suture. The wound was cleaned, the membrane sewn with 4.0 dissolvable Vicryl suture and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation was evaluated using testing with von Frey filaments. As described previously by S. R. Chaplan, et al. ("Quantitative assessment of tactile allodynia in the rat paw" J. Neurosci. Meth. (1994) vol. 53 pp. 55-63), two weeks following surgery rats were acclimated to a testing box constructed of plexiglass with a wire mesh floor which allowed access to the plantar surface of the animal's hindpaws. Using an Up-Down method (Dixon, Annu. Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63), von Frey filaments of increasing stiffness were applied to the plantar surface of the hindpaws and the withdrawal response of the animals was observed; for the surgically affected paw with neuropathic pain (the left side paw) the baseline level of allodynia has a withdrawal threshold of ≦4 g of pressure. By comparison, for the control paw without allodynia (in this case the right side paw), the typical withdrawal pressure is around 15 g. Representative compounds of the invention, administered intraperitoneally 30 minutes before testing, are able to reduce the symptoms of neuropathic pain and induce a dose-dependent increase in the withdrawal threshold for allodynic (left side) limb, up to a maximum effect of 15 g. The efficacy of the compound in reducing neuropathic pain at different doses is determined by comparing response in the surgery-affected paw versus the response in the control paw. This is expressed as the MPE (maximum percent effect), or 100 times the withdrawal threshold of the allodynic (left side) divided by the withdrawal threshold of the control (right side).

Determination of Analgesic Effect Against Inflammatory Pain

To assess the effectiveness of representative compounds of the invention against acute model inflammatory pain, animals were tested in an acute model of carrageenan-induced thermal hyperalgesia (see for example, Honore, et al. *Behavioural Brain Research* 167 (2006) 355-364; Porreca, et al Journal of Pharmacology and Experimental Therapeutics (2006) vol. 318 pp. 195-205). Carrageenan was injected into the test paw of the animal, and after 90 minutes, the test drug was administered by intraperitoneal dosing; the effect on thermal hyperalgesia was assessed in a hotbox assay which was done 30 minutes after the intraperitoneal dosing of the test drug, and the MPE (maximal percent effect) reported by comparison to the control paw (not injected with carrageenan), according to 100 times the withdrawal latency of the carrageenan injected paw (in seconds) divided by the withdrawal latency of the control (not injected with carrageenan) paw.

Determination of Analgesic Effect Against Pain in a Surgical Skin Incision Model This is a surgical skin incision model (Joshi, et al. Pain 123 (2006) 75-82). Animals (rats) were prepared for testing by subjecting them in a surgical procedure carried out under sterile conditions, where the plantaris muscle was elevated and incised longitudinally with the origin and insertion of the muscle remaining intact. The skin was then closed with two mattress sutures (e.g. 5-0 nylon sutures). After surgery, animals were allowed to recover on a warming plate and housed individually in cages with soft bedding. After this surgery, the animals develop a hypersensitivity called allodynia; allodynia is pain due to a stimulus that does not normally provoke pain. Animals were tested for mechanical allodynia using von Frey hair mechanical stimulation 2, 24, and 48 hours after surgery as described for the Chung model.

Compounds of the invention are histamine $H_4$ receptor ligands that modulate function of the histamine $H_4$ receptor by altering the activity of the receptor. These compounds may be antagonists that block the action of receptor activation induced by histamine $H_4$ receptor agonists such as histamine; they may be histamine $H_4$ receptor inverse agonists that inhibit the basal activity of the receptor and block the action of receptor activation induced by histamine $H_4$ receptor agonists such as histamine, and they may be partial agonists that partially block the action of receptor activation induced by histamine $H_4$ receptor agonists such as histamine and prevent full activation of histamine $H_4$ receptors.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:
1. A compound of formula (I):

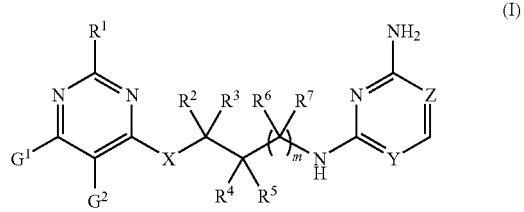

or a pharmaceutically acceptable salt, wherein:
X is NH, NCH$_3$, or O;
Y is N or CR$^8$;
Z is N or CR$^9$;
R$^1$ is selected from hydrogen, NH$_2$, alkyl, or fluoroalkyl;
R$^2$, R$^3$, R$^4$, R$^5$, R$^6$, and R$^7$ are each independently selected from the group consisting of hydrogen, alkoxycarbonyl, alkyl, alkylcycloalkyl, carboxy, cyano, cyanoalkyl, cycloalkoxyalkyl, cycloalkyl, fluoroalkoxy, fluoroalkyl, fluorocycloalkyl, fluorocycloalkylalkyl, fluorine, formyl, haloalkoxy, hydroxyalkyl, and C(O)NR$^{10}$R$^{11}$; or
R$^2$ and R$^3$, or R$^4$ and R$^5$, or R$^6$ and R$^7$ taken together are —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$OCH$_2$CH$_2$—, —CH$_2$OCH$_2$CH$_2$—, or —OCH$_2$CH$_2$CH$_2$—; or
R$^3$ and R$^4$, or R$^5$ and R$^6$ taken together are —CH$_2$CH$_2$CH$_2$—, —CH$_2$CH$_2$CH$_2$CH$_2$—, or —CH$_2$OCH$_2$—;
R$^8$ and R$^9$ are each independently selected from the group consisting of hydrogen, fluoroalkyl, and halogen;
R$^{10}$ and R$^{11}$ are each independently selected from the group consisting of hydrogen and alkyl;
G$^1$ and G$^2$ are taken together to form groups of formula (ii) or formula (iv)

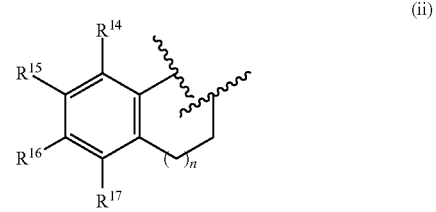

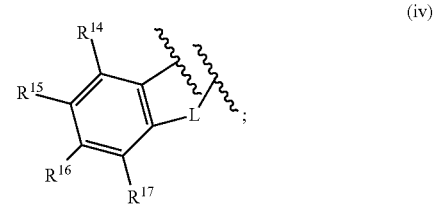

L is selected from O, S, NH, or N—CH$_3$;
R$^{12}$ and R$^{13}$ are each independently selected from the group consisting of hydrogen, alkyl, aryl, and arylalkyl;

$R^{14}$, $R^{15}$, $R^{16}$, and $R^{17}$ are each independently selected from the group consisting of hydrogen, acyl, acyloxy, alkenyl, alkoxy, alkoxyalkoxy, alkoxyalkyl, alkoxycarbonyl, alkoxyimino, alkoxysulfonyl, alkyl, alkylcycloalkyl, alkylsulfonyl, alkylthio, alkynyl, amido, aryl, halogen, fluoroalkyl, carboxy, cyano, cyanoalkyl, cycloalkoxyalkyl, cycloalkyl, fluoroalkoxy, fluorocycloalkyl, fluorocycloalkylalkyl, formyl, haloalkoxy, haloalkyl, heteroaryl, heterocycle, hydroxy, hydroxyalkyl, mercapto, nitro, $C(O)NR^{25}R^{26}$, $NR^{25}C(O)$alkyl, —$NR^{26}C(O)O$alkyl, $N(R^{25})SO_2(R^{26})$, —$NR^{25}R^{26}$, O-aryl, O-heteroaryl, S-aryl, and —$SO_2(NR^{25}R^{26})$; or $R^{15}$ and $R^{16}$ taken together are: —$CH_2CH_2CH_2$—, —$CH_2CH_2CH_2CH_2$—, —$CH_2OCH_2$—, or —$OCH_2CH_2$—;

$R^{25}$ and $R^{26}$ are independently selected from the group consisting of hydrogen, acyl, alkoxyalkyl, alkyl, aryl, arylalkyl, cyanoalkyl, cycloalkyl, cycloalkoxyalkyl, cycloalkylalkyl, fluoroalkyl, fluorocycloalkylalkyl, and hydroxyalkyl;

m is 0, or 1; and n is 0, 1, 2, or 3.

2. The compound of claim 1, wherein $G^1$ and $G^2$ taken together are a group of formula (iv)

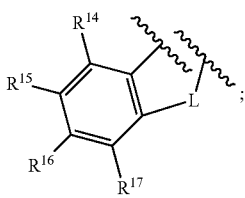

(iv)

L is O, S, NH, or N—CH$_3$; and
$R^1$ is hydrogen or NH$_2$.

3. The compound according to claim 2 wherein the compound is $N^4$-[2([1]benzofuro[3,2-c]pyrimidin-4-ylamino)ethyl]pyrimidine-2,4-diamine.

4. The compound of claim 1, wherein $G^1$ and $G^2$ taken together are a group of formula

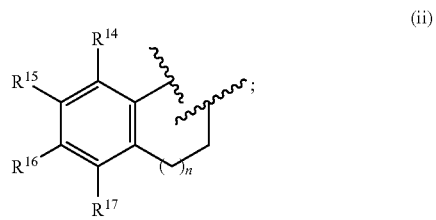

(ii)

n is 0, 1 or 2; and
$R^1$ is hydrogen or NH$_2$.

5. The compound according to claim 4 wherein the compound is:

$N^4$-{2-[(2-aminopyrimidin-4-yl)amino]ethyl}-6,7-dihydro-5H-benzo[6,7]cyclohepta[1,2-d]pyrimidine-2,4-diamine;

$N^4$-{2-[(2-aminopyrimidin-4-yl)amino]ethyl}-$N^4$-methyl-6,7-dihydro-5H-benzo[6,7]cyclohepta[1,2-d]pyrimidine-2,4-diamine;

$N^4$-{3-[(2-aminopyrimidin-4-yl)amino]propyl}-6,7-dihydro-5H-benzo[6,7]cyclohepta[1,2-d]pyrimidine-2,4-diamine; or $N^4$-{2-[(4-aminopyrimidin-2-yl)amino]ethyl}-6,7-dihydro-5H-benzo[6,7]cyclohepta[1,2-d]pyrimidine-2,4-diamine.

6. A pharmaceutical composition comprising a compound of claim 1 and a pharmaceutically acceptable carrier.

* * * * *